US008222311B2

(12) United States Patent
Masuda et al.

(10) Patent No.: US 8,222,311 B2
(45) Date of Patent: Jul. 17, 2012

(54) HYDROXYALKYLATED POLYALKYLENEPOLYAMINE COMPOSITION, METHOD OF PRODUCING THE SAME AND THEIR USE IN POLYURETHANES

(75) Inventors: Takahiro Masuda, Shunan (JP); Yutaka Tamano, Shunan (JP)

(73) Assignee: Tosoh Corporation, Shunan-shi (JP)

( * ) Notice: Subject to any disclaimer, the term of this patent is extended or adjusted under 35 U.S.C. 154(b) by 1224 days.

(21) Appl. No.: 11/718,289

(22) PCT Filed: Nov. 1, 2005

(86) PCT No.: PCT/JP2005/020133
§ 371 (c)(1),
(2), (4) Date: Apr. 30, 2007

(87) PCT Pub. No.: WO2006/049182
PCT Pub. Date: May 11, 2006

(65) Prior Publication Data
US 2008/0004362 A1 Jan. 3, 2008

(30) Foreign Application Priority Data

Nov. 2, 2004 (JP) ................................. 2004-319484
Feb. 25, 2005 (JP) ................................. 2005-050363

(51) Int. Cl.
*C08G 18/32* (2006.01)
(52) U.S. Cl. ........ 521/164; 521/117; 521/128; 521/129; 521/130; 521/167; 521/170; 528/49; 528/53
(58) Field of Classification Search .................. 521/117, 521/128, 129, 130, 164, 167, 170; 528/49, 528/53
See application file for complete search history.

(56) References Cited

U.S. PATENT DOCUMENTS

| | | | |
|---|---|---|---|
| 548,816 A | 10/1895 | Paul | |
| 2,395,400 A | 2/1946 | De. Groote et al. | |
| 2,901,461 A | 8/1959 | Auerbach et al. | |
| 3,092,609 A | 6/1963 | Kostelitz et al. | |
| 4,026,840 A | 5/1977 | Bechara et al. | |
| 4,175,097 A | 11/1979 | McEntire | |
| 4,248,930 A | 2/1981 | Haas et al. | |
| 4,430,455 A | 2/1984 | Raden et al. | |
| 5,105,013 A | 4/1992 | Tanis et al. | |
| 5,229,430 A * | 7/1993 | Tamano et al. ............... | 521/129 |
| 5,430,190 A * | 7/1995 | Carr et al. .................... | 564/477 |
| 5,633,293 A * | 5/1997 | Van Court Carr et al. .... | 521/118 |
| 6,723,819 B2 * | 4/2004 | Masuda et al. ................ | 528/52 |
| 2012/0041088 A1 * | 2/2012 | Ishida et al. .................. | 521/129 |

FOREIGN PATENT DOCUMENTS

| | | |
|---|---|---|
| DE | 868 300 C | 2/1953 |
| DE | 27 39 353 A1 | 5/1978 |
| DE | 3 135 065 A1 | 3/1983 |
| EP | 0 074 537 A1 | 3/1983 |
| EP | 0 375 333 A2 | 6/1990 |
| EP | 0 414 574 A2 | 2/1991 |
| EP | 0 587 221 A1 | 3/1994 |
| FR | 2 367 734 | 5/1978 |
| GB | 1338275 | 11/1973 |
| GB | 1 561 617 | 2/1980 |
| JP | 43-26083 | 9/1968 |
| JP | 46-4846 | 11/1971 |
| JP | 52-54738 | 5/1977 |
| JP | 53-50110 | 5/1978 |
| JP | 58-55448 | 4/1983 |
| JP | 60-112743 | 6/1985 |
| JP | 61-31727 B2 | 7/1986 |
| JP | 61-236751 | 10/1986 |
| JP | 63-265909 | 11/1988 |

(Continued)

OTHER PUBLICATIONS

Keiji Iwata, "Polyurethane Resin Handbook", Nikkan kogyou Shinbun, Ltd.( First Edition), 1987, pp. 118-122. (with partial English translation).
Supplementary Search Report issued Jan. 20, 2011 in European Patent Application No. 05805486.7-2103 1813599.

(Continued)

*Primary Examiner* — John Cooney
(74) *Attorney, Agent, or Firm* — Oblon, Spivak, McClelland, Maier & Neustadt, L.L.P.

(57) ABSTRACT

Disclosed is a novel hydroxyalkylated polyalkylene polyamine composition, and a method for preparing the hydroxyalkylated polyalkylene polyamine composition at low cost. Further disclosed is a method for producing a polyurethane resin by using the hydroxyalkylated polyalkylene polyamine composition containing at least two hydroxyalkylated polyalkylene polyamines represented by the following general formula (1):

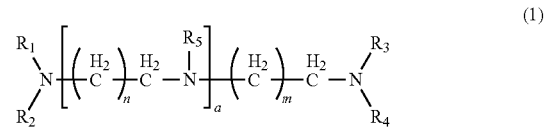

In the formula (1), $R_1$ to $R_5$ are independently a $C_1$ to $C_3$ alkyl group or a substituent represented by the following general formula (2):

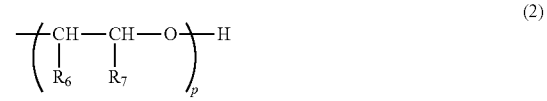

wherein $R_6$ and $R_7$ are independently a hydrogen atom or a $C_1$ to $C_4$ alkyl group, and p is an integer from 1 to 3; and $R_5$ and $R_1, R_2, R_3,$ or $R_4$ may arbitrarily bond together to form a ring; at least one of $R_1$ to $R_5$ is a substituent represented by the general formula (2) but all of $R_1$ to $R_5$ cannot be substituents represented by the general formula (2) at the same time; n and m are independently an integer from 1 to 5; and a is an integer from 1 to 6.

24 Claims, No Drawings

FOREIGN PATENT DOCUMENTS

| | | |
|---|---|---|
| JP | 2-243654 | 9/1990 |
| JP | 3-83955 | 4/1991 |
| JP | 4-346965 | 12/1992 |
| JP | 05-214091 | 8/1993 |
| JP | 2003-073439 | 3/2003 |
| JP | 2003105052 | 4/2003 |

OTHER PUBLICATIONS

Notice of Reasons for Rejection dated Aug. 9, 2011. (w/English Translation).

Notice of Reasons for Rejection dated Nov. 1, 2011. (w/English Translation).

* cited by examiner

HYDROXYALKYLATED POLYALKYLENEPOLYAMINE COMPOSITION, METHOD OF PRODUCING THE SAME AND THEIR USE IN POLYURETHANES

TECHNICAL FIELD

The present invention relates to a hydroxyalkylated polyalkylene polyamine composition containing at least one tertiary amino group such as a methyl amino group and a dimethyl amino group (hereinafter may be generically referred to as tertiary amino group), a method for preparing the same, and a method for preparing a polyurethane resin using the hydroxyalkylated polyalkylene polyamine composition.

The hydroxyalkylated polyalkylene polyamine composition of the present invention is useful as an epoxy curing agent, an urethane raw material, a surfactant, a fiber processing agent, a paper reinforcing agent, a resin modifier, a lubricating oil additive, and the like. In particular, it is especially useful as a composition for preparing a polyurethane resin or polyurethane foam which has little volatile amine catalyst and harmful metal catalyst when preparing a polyurethane resin. Since the hydroxyalkylated polyalkylene polyamine composition of the present invention has catalytic ability, the amount of conventional amine catalysts used can be reduced and a polyurethane resin can be produced with excellent productivity.

Also, the present invention relates to a method for preparing a rigid polyurethane foam using a hydroxyalkylated polyalkylene polyamine composition which includes at least one tertiary amino group such as a methyl amino group and a dimethyl amino group.

In the method for preparing a rigid polyurethane foam of the present invention, since a harmful metal catalyst is hardly used and the amount of a volatile amine catalyst used does not increase, the present invention is industrially extremely useful as a method for preparing a rigid polyurethane foam which does not worsen the work environment and which does not cause toxicity problems or environmental problems by the heavy metals which remain in the product.

Priority is claimed on Japanese Patent Application No. 2004-319484, filed on Nov. 2, 2004, and Japanese Patent Application No. 2005-050363, filed on Feb. 25, 2005, the contents of which are incorporated herein by reference.

BACKGROUND ART

Polyurethane resins are produced by reacting a polyol and a polyisocyanate in the presence of a catalyst and as required by necessity, a blowing agent, a surfactant, a flame retardant, a cross-linking agent, and/or the like. The use of many metallic compounds and tertiary amine compounds as the catalyst in the manufacture of polyurethane resins is known. These catalysts are heavily used industrially either alone or in combination.

In the manufacture of polyurethane foam using water and/or a low-boiling point organic compound as the blowing agent, a tertiary amine compound is particularly widely used among these catalysts since it has excellent productivity and moldability. Examples of such a tertiary amine compound include conventionally well-known triethylenediamine, N,N,N',N'-tetramethyl-1,6-hexanediamine, bis(2-dimethylaminoethyl)ether, N,N,N',N'',N''-pentamethyl diethylenetriamine, N-methyl morpholine, N-ethyl morpholine, N,N-dimethylethanolamine (for example, refer to Non-Patent Document 1). In most cases, metallic compounds are combined with tertiary amines and not used alone since productivity and moldability worsen.

The above-mentioned tertiary amine catalyst gradually discharges as a volatile amine from a polyurethane product and, for example, an odor problem is caused by the volatile amine in interior materials of vehicles and the like, and a discoloration problem of other materials such as vinyl chloride is caused. Also, generally tertiary amine catalysts have a strong odor and the work environment at the time of polyurethane resin manufacture becomes remarkably worse. As methods for solving the problems relating to these volatile tertiary amines, the use of amine catalysts which have at least one primary or secondary amino group or at least one hydroxyl group in the molecule that can react with a polyisocyanate (hereinafter may also referred to as reactive catalyst) and the use of a bifunctional cross-linking agent which includes a tertiary amino group in the molecule have been proposed (refer to Patent Documents 1-4).

It is said that the above-mentioned problems may be avoided by using the above-mentioned methods utilizing a reactive catalyst, since the reactive catalyst is fixed in the polyurethane resin backbone in the form of reacting with polyisocyanate. Although the methods may be effective in reducing the odor in the final resin product, these methods cannot be used as methods to improve the work environment at the time of polyurethane resin manufacture since these amine catalysts are volatile. Also, there is a problem that the physical properties of the polyurethane resin such as hardness are reduced.

Furthermore, although the above-mentioned method using a cross-linking agent is effective in reducing the odor in the final resin product and improving the work environment at the time of polyurethane resin manufacture, the physical properties of the polyurethane resin such as hardness are insufficient.

On the other hand, an alkylene oxide adduct of N,N-dimethyldipropylenetriamine and the like has been proposed as a trifunctional polyol including a tertiary amino group in its molecule (for example, refer to Patent Document 5). This polyol has three hydroxyl groups in its molecule and although there is potential that the above-mentioned problems can be solved, the cost of raw material compounds when preparing this polyol is expensive. Thus, there are problems such as high preparing costs when this is used in the manufacture of a polyurethane resin.

Also, many alkylene oxide adducts of ethylene diamine are commercially available in order to reduce the amount of the tertiary amine catalyst used (hereinafter may also referred to as amine polyols). Although these amine polyols only have a little unpleasant odor and are effective in improving the work environment since the amount of the tertiary amine catalyst used can be reduced, their catalytic activity is small and as a result, it is necessary to use a large quantity thereof. Thus, there are problems such as reduction in the flame retardancy of the rigid polyurethane foam.

On the other hand, although metallic catalysts do not cause the odor problem and the problem of degrading other materials like the tertiary amines, when a metallic catalyst is used alone, productivity, physical properties, and moldability worsen as described above and furthermore, the toxicity problem and environmental problems by the heavy metals which remain in the product have received attention. For example, although dibutyltin dilaurate or lead octanoate is used in the manufacture of a spray-type rigid polyurethane foam by which polyurethane foam is formed by being discharging in a mixture by a spray, a substitute for these is strongly desired.

Patent Document 1: Japanese Unexamined Patent Application, First Publication No. S46-4846

Patent Document 2: Japanese Examined Patent Application, Second Publication No. S61-31727

Patent Document 3: Japanese Patent No. 2971979

Patent Document 4: Japanese Unexamined Patent Application, First Publication No. S63-265909

Patent Document 5: Japanese Unexamined Patent Application, First Publication No. H5-214091

Non-Patent Document 1: Keiji Iwata "Polyurethane Resin Handbook", page 118, (First Edition 1987) Nikkan Kogyou Shinbun, Ltd.

DISCLOSURE OF THE INVENTION

The present invention has been achieved in consideration of the above-mentioned circumstances, and an object of the present invention is to provide a novel hydroxyalkylated polyalkylene polyamine composition, an inexpensive manufacturing method thereof, and a method for preparing a polyurethane product using the hydroxyalkylated polyalkylene polyamine composition without causing an odor problem, toxicity and environmental problems and which has excellent productivity and moldability, and furthermore, a method for preparing a rigid polyurethane product without causing an odor problem, toxicity and environmental problems and for which excellent moldability can be obtained.

The present invention has been completed as a result of extensive research by the inventors in order to solve the above-mentioned problems.

In other words, the present invention is the below-mentioned hydroxyalkylated polyalkylene polyamine composition, method for preparing the same, and method for preparing a polyurethane resin using the hydroxyalkylated polyalkylene polyamine composition.

<1> A hydroxyalkylated polyalkylene polyamine composition, including: at least two hydroxyalkylated polyalkylene polyamines represented by the following general formula (1):

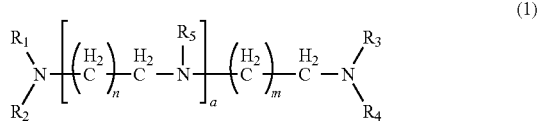

wherein $R_1$ to $R_5$ are independently a $C_1$ to $C_3$ alkyl group or a substituent represented by the following general formula (2):

wherein $R_6$ and $R_7$ are independently a hydrogen atom or a $C_1$ to $C_4$ alkyl group, and p is an integer from 1 to 3, and $R_5$ and $R_1$, $R_2$, $R_3$, or $R_4$ may arbitrarily bond together to form a ring; at least one of $R_1$ to $R_5$ is a substituent represented by the general formula (2) but all of $R_1$ to $R_5$ cannot be substituents represented by the general formula (2) at the same time; n and m are independently an integer from 1 to 5; and a is an integer from 1 to 6.

<2> A hydroxyalkylated polyalkylene polyamine composition according to <1>, wherein the ratio of $C_1$ to $C_3$ alkyl groups to substituents represented by the general formula (2) among $R_1$ to $R_5$ in the general formula (1) is in the range of ($C_1$ to $C_3$ alkyl groups)/(substituents represented by the general formula (2))=80/20 to 20/80 (molar ratio).

<3> A hydroxyalkylated polyalkylene polyamine composition according to <1> or <2>, wherein a hydroxyl value is 20 to 800 mg KOH/g.

<4> A N-hydroxyalkylated polyalkylene polyamine composition, including: at least two hydroxyalkylated polyalkylene polyamines represented by the following general formula (3):

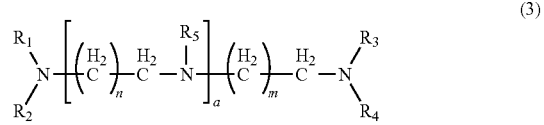

wherein $R_1$ to $R_5$ are independently a hydrogen atom or a $C_1$ to $C_3$ alkyl group, when $R_5$ is a $C_1$ to $C_3$ alkyl group, $R_5$ and $R_1$, $R_2$, $R_3$, or $R_4$ may arbitrarily bond together to form a ring; at least one of $R_1$ to $R_5$ is a hydrogen atom; n and m are independently an integer from 1 to 5; and a is an integer from 1 to 6.

<5> A hydroxyalkylated polyalkylene polyamine composition according to <4> wherein the ratio of $C_1$ to $C_3$ alkyl groups to hydrogen atoms is in the range of ($C_1$ to $C_3$ alkyl groups)/(hydrogen atoms)=80/20 to 20/80 (molar ratio).

<6> A method for preparing the N-hydroxyalkylated polyalkylene polyamine composition of <4> or <5>, including: partially N-alkylating a polyalkylene polyamine represented by the following general formula (4) by a $C_1$ to $C_3$ alkylating agent:

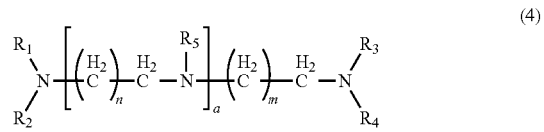

wherein $R_1$ to $R_4$ are hydrogen atoms; $R_5$ is a hydrogen atom or a $C_1$ to $C_3$ alkyl group; when $R_5$ is a $C_1$ to $C_3$ alkyl group, $R_5$ and $R_1$, $R_2$, $R_3$, or $R_4$ may arbitrarily bond together to form a ring; n and m are independently an integer from 1 to 5; and a is an integer from 1 to 6.

<7> A method for preparing the N-hydroxyalkylated polyalkylene polyamine composition according to <6>, wherein the alkylating agent is formaldehyde.

<8> A method for preparing the N-hydroxyalkylated polyalkylene polyamine composition according to <6> or <7>, wherein the polyalkylene polyamine represented by the general formula (4) is selected from the group consisting of diethylenetriamine, dipropylenetriamine, dihexamethylenetriamine, triethylenetetramine, tripropylene tetramine, tetraethylenepentamine, pentaethylenehexamine, N-aminoethyl piperazine, N-2(2'-aminoethyl)aminoethyl piperazine, N,N'-bis(2-aminoethyl) piperazine, N-2(2'(2"-aminoethyl)aminoethyl)aminoethyl piperazine, N-2(2'-aminoethyl)aminoethyl-N'-aminoethyl piperazine, N,N'-bis(3-aminopropyl) piperazine, tris(2-aminoethyl)amine, tris(3-aminopropyl) amine, N,N-bis(2-aminoethyl)diethylenetriamine, and N"-bis(2-aminoethyl)-N-aminoethyl piperazine.

<9> A method for preparing the hydroxyalkylated polyalkylene polyamine composition of any one of <1> to <3>, including: oxyalkylating the N-hydroxyalkylated polyalkylene polyamine composition of <4> or <5> by a $C_2$ to $C_4$ alkylene oxide.

<10> A method for preparing the hydroxyalkylated polyalkylene polyamine composition according to <9>, wherein the alkylene oxide is one or more selected from the group consisting of ethylene oxide, 1,2-propylene oxide, and 1,2-butylene oxide.

<11> A method for preparing the hydroxyalkylated polyalkylene polyamine composition of any one of <1> to <3>, including: partially N-alkylating a polyalkylene polyamine represented by the following general formula (4) by a $C_1$ to $C_3$ alkylating agent; and then oxyalkylating by a $C_1$ to $C_4$ alkylene oxide:

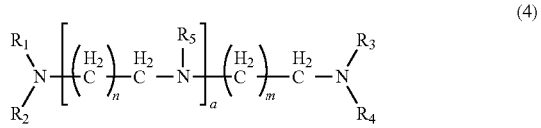

wherein $R_1$ to $R_4$ are hydrogen atoms, $R_5$ is a hydrogen atom or a $C_1$ to $C_3$ alkyl group; when $R_5$ is a $C_1$ to $C_3$ alkyl group, $R_5$ and $R_1$, $R_2$, $R_3$, or $R_4$ may arbitrarily bond together to form a ring; n and m are independently an integer from 1 to 5; and a is an integer from 1 to 6.

<12> A method for preparing the hydroxyalkylated polyalkylene polyamine composition according to <11>, wherein the alkylating agent is formaldehyde.

<13> The method for preparing the hydroxyalkylated polyalkylene polyamine composition according to <11> or <12>, wherein the polyalkylene polyamine represented by the general formula (4) is selected from the group consisting of diethylenetriamine, dipropylenetriamine, dihexamethylentriamine, triethylenetetramine, tripropylene tetramine, tetraethylenepentamine, pentaethylenehexamine, N-aminoethyl piperazine, N-2(2'-aminoethyl)aminoethyl piperazine, N,N'-bis(2-aminoethyl) piperazine, N-2(2'(2"-aminoethyl)aminoethyl)aminoethyl piperazine, N-2(2'-aminoethyl)aminoethyl-N'-aminoethyl piperazine, N,N'-bis(3-aminopropyl) piperazine, tris(2-aminoethyl)amine, tris(3-aminopropyl) amine, N,N-bis(2-aminoethyl)diethylenetriamine, and N"-bis (2-aminoethyl)-N-aminoethyl piperazine.

<14> A method for preparing a polyurethane resin, including: reacting a polyol and an isocyanate in the presence of the hydroxyalkylated polyalkylene polyamine composition of any one of <1> or <3>.

<15> A method for preparing a polyurethane resin, including: reacting a polyol and an isocyanate in the presence of the hydroxyalkylated polyalkylene polyamine composition obtained by the preparing method of any one of <9> to <13>.

<16> A method for preparing a polyurethane foam, including: reacting a polyol and an isocyanate in the presence of the hydroxyalkylated polyalkylene polyamine composition according to any one of <1> to <3> and a blowing agent.

<17> A method for preparing a polyurethane foam, including: reacting a polyol and an isocyanate in the presence of the hydroxyalkylated polyalkylene polyamine composition obtained by the preparing method of any one of <9> to <13> and a blowing agent.

<18> A method for preparing a polyurethane foam according to <16> or <17>, wherein water and/or an organic compound having a low boiling point are/is used as the blowing agent.

<19> A method for preparing a rigid polyurethane foam, including: reacting a polyol and a isocyanate in the presence of a blowing agent, a catalyst, and a foam stabilizing agent, wherein the hydroxyalkylated polyalkylene polyamine composition of any one of <1> to <3> is used as the polyol, a tertiary amine compound having at least one active hydrogen group in its molecule is used as the catalyst, and at least 1 part by weight of water relative to 100 parts by weight of the polyol is used as the blowing agent.

<20> A method for preparing a rigid polyurethane foam, including: reacting a polyol and a isocyanate in the presence of a blowing agent, a catalyst, and a foam stabilizing agent, wherein the hydroxyalkylated polyalkylene polyamine composition obtained by the method of any one of <9> to <13> is used as the polyol, a tertiary amine compound having at least one active hydrogen group in its molecule is used as the catalyst, and at least 1 part by weight of water relative to 100 parts by weight of the polyol is used as the blowing agent.

<21> A method for preparing a rigid polyurethane foam according to <19> or <20>, wherein the hydroxyl value of the hydroxyalkylated polyalkylene polyamine composition is in the range from 100 to 800 mg KOH/g.

<22> A method for preparing a rigid polyurethane foam according to any one of <19> to <21>, wherein the tertiary amine compound having at least one active hydrogen group in its molecule is selected from the group consisting of N'-(2-hydroxyethyl)-N,N,N'-trimethyl-bis(2-aminoethyl)ether, N,N-dimethyl hexanol amine, N,N-dimethylamino ethoxy ethanol, N,N,N'-trimethyl-N'-(2-hydroxyethyl)ethylenediamine, N-(2-hydroxyethyl)-N,N',N",N"-tetramethyldiethylenetriamine, N-(2-hydroxypropyl)-N,N',N",N"-tetramethyldiethylenetriamine, N,N,N'-trimethyl-N'-(2-hydroxyethyl) propanediamine, N-methyl-N'-(2-hydroxyethyl) piperazine, bis(N,N-dimethylaminopropyl)amine, bis(N,N-dimethylaminopropyl)isopropanolamine, 2-amino quinuclidine, 3-amino quinuclidine, 4-amino quinuclidine, 2-quinuclidiol, 3-quinuclidinol, 4-quinuclidinol, 1-(2'-hydroxypropyl)imidazole, 1-(2'-hydroxypropyl)-2-methylimidazole, 1-(2'-hydroxyethyl)imidazole, 1-(2'-hydroxyethyl)-2-methylimidazole, 1-(2'-hydroxypropyl)-2-methylimidazole, 1-(3'-aminopropyl)imidazole, 1-(3'-aminopropyl)-2-methylimidazole, 1-(3'-hydroxypropyl)imidazole, 1-(3'-hydroxypropyl)-2-methylimidazole, N,N-dimethylaminopropyl-N'-(2-hydroxyethyl)amine, N,N-dimethylaminopropyl-N',N'-bis(2-hydroxyethyl)amine, N,N-dimethylaminopropyl-N',N'-bis(2-hydroxypropyl) amine, N,N-dimethylaminoethyl-N',N'-bis(2-hydroxyethyl) amine, and N,N-dimethylaminoethyl-N',N'-bis(2-hydroxypropyl)amine.

<23> A method for preparing a rigid polyurethane foam according to any one of <19> to <21>, wherein the tertiary amine compound having at least one active hydrogen group in its molecule is selected from the group consisting of N'-(2-hydroxyethyl)-N,N,N'-trimethyl-bis(2-aminoethyl)ether, N,N-dimethylaminoethoxyethanol, N,N,N'-trimethyl-N'-(2-hydroxyethyl)ethylenediamine, N-(2-hydroxyethyl)-N,N',N",N"-tetramethyldiethylenetriamine, N-(2-hydroxypropyl)-N,N',N",N"-amine, and bis(N,N-dimethylaminopropyl)isopropanolamine.

<24> The method for preparing a rigid polyurethane foam according to any one of <19> to <23>, wherein the rigid polyurethane foam is a spray-type rigid polyurethane foam.

EFFECT OF THE INVENTION

According to the present invention, novel hydroxyalkylated polyalkylene polyamine composition, an inexpensive manufacturing method thereof, and a method for producing a polyurethane resin are provided.

Since the hydroxyalkylated polyalkylene polyamine composition of the present invention has a plurality of hydroxyl groups, a relatively high molecular weight, and catalytic activity, it becomes possible to reduce the amount of conventional amine catalyst used without deteriorating the physical properties of a polyurethane resin when the composition is used for the manufacturing method of the polyurethane. In addition, it becomes possible to obtain polyurethane products with excellent productivity and moldability at low cost without causing odor problems or toxic and environmental problems.

Also, according to the method of manufacturing rigid polyurethane foam of the present invention, it becomes possible to obtain rigid polyurethane foam products with excellent productivity without causing the above-mentioned odor problems or toxic and environmental problems.

BEST MODE FOR CARRYING OUT THE INVENTION

They hydroxyalkylated polyalkylene polyamine composition of the present invention includes two or more kinds of hydroxyalkylated polyalkylene polyamine represented by the above general formal (1). It is difficult to manufacture only one kind of the hydroxyalkylated polyalkylene polyamine represented by the above formula (1) at low cost, and products of the present invention may be manufactured at low cost by using two or more kinds of hydroxyalkylated polyalkylene polyamines.

In the above general formula (1), a represents an integer of 1 to 6. If the molecular weight is too small, the reactivity of hydroxyalkylated polyalkylene polyamine becomes low. Also, the larger the value of a, the higher the boiling point of primary or secondary amine raw material and industrial purification of the raw material becomes difficult. Accordingly, the range of a is preferably between 2 and 5.

In the above general formula (1), m and n each independently represent an integer of 1 to 5. The larger the values of m and n, the better the moldability of polyurethane resin product obtained when the polyamine is used for the production thereof but the reactivity of hydroxyalkylated polyalkylene polyamine becomes low. In order to industrially produce it at low cost, it is preferable that m and n each independently being in the range of 1 to 2.

In the above general formula (2), the value of p is an integer of 1 to 3. The larger the value of p, the lower the reactivity and viscosity of the terminal hydroxyl group.

Although the hydroxyalkylated polyalkylene polyamine composition of the present invention is not particularly limited, it is preferably in the range of 20 to 800 mg KOH/g, and more preferably in the range of 100 to 700 mg KOH/g.

Note that the hydroxyl value of the hydroxyalkylated polyalkylene polyamine composition in the present invention means the hydroxyl value per average molecular weight of the composition, and may be defined by the following equation:

Hydroxyl value (mg/KOH)=No. of OH groups in a molecule/average molecular weight×56.11×1000

The hydroxyalkylated polyalkylene polyamine composition of the present invention may be readily prepared by using known methods described in documents.

For example, the hydroxyalkylated polyalkylene polyamine composition may be produced by partially N-alkylating the polyalkylene polyamine represented by the above general formula (4) using N-alkylating agent such as monoalcohols, aldehydes, and halogenated alkyls, to obtain an N-alkylene polyamine composition which includes two or more kinds of N-alkylated polyalkylene polyamine represented by the above general formula (3), and further adding an alkylene oxide to the position of the active hydrogen of the N-alkylene polyamine composition.

Also, the hydroxyalkylated polyalkylene polyamine composition of the present invention may be produced by adding an alkylene oxide to the position of the active hydrogen of the N-alkylated polyalkylene polyamine composition represented by the above general formula (3).

In the method of the present invention, the ratio of alkylation and oxyalkylation relates to the production rate (i.e., curing rate) of polyurethane obtained when the hydroxyalkylated polyalkylene polyamine composition of the present invention is used for the production of polyurethane and to the inhibition of volatile amines. For example, when the ratio of oxyalkylation increases, the curing rate of the polyurethane resin decreases although the amount of volatile amines produced is reduced. On the other hand, when the ratio of oxyalkylation decreases, the amount of volatile amines produced increases and the hardness of the polyurethane resin is reduced although the curing rate of the polyurethane resin increases. Accordingly, alkylation in the range of 20 to 80% by molar ratio with respect to the active hydrogen groups of polyalkylene polyamine represented by the above general formula (4) is preferable, and alkylation in the range of 30 to 70% is more preferable.

That is, in the above general formula (3), it is preferable that the ratio of alkyl groups having the number of carbon atoms of 1 to 3 to the hydrogen atoms among $R_1$ to $R_5$ is preferably in the range of ($C_1$ to $C_3$ alkyl groups)/(hydrogen atoms)=80/20 to 20/80 (molar ratio), and more preferably in the range of 70/30 to 30/70 (molar ratio).

Also, in the above general formula (1), it is preferable that the ratio of alkyl groups having the number of carbon atoms of 1 to 3 to the substituents represented by the general formula (2) among $R_1$ to $R_5$ is preferably in the range of ($C_1$ to $C_3$ alkyl groups)/(substituents represented by the general formula (2))=80/20 to 20/80 (molar ratio), and more preferably in the range of 70/30 to 30/70 (molar ratio). The hydroxyalkylated polyalkylene polyamine composition of the present invention may be efficiently produced by adjusting, in the general formula (1), the ratio of alkyl groups having the number of carbon atoms of 1 to 3 to the substituents represented by the general formula (2) among $R_1$ to $R_5$ to be ($C_1$ to $C_3$ alkyl groups)/(substituents represented by the general formula (2))=80/20 to 20/80 (molar ratio).

In the method of the present invention, the polyalkylene polyamine represented by the above general formula (4) is not particularly limited. Specific examples thereof include diethylene triamine, dipropylene triamine, dihexamethylene triamine, triethylene tetramine, tripropylenetetramine, tetraethylene pentamine, pentaethylene hexamine, N-amino ethylpiperazine, N-2(2'-amino ethyl)amino ethylpiperazine, N,N'-bis(2-amino ethyl)piperazine, N-2(2'(2"-amino ethyl)amino ethyl)amino ethylpiperazine, N-2(2'-amino ethyl)aminoethyl-N'-amino ethylpiperazine, N,N'-bis(3-aminopropyl) piperazine, tris (2-amino ethyl)amine, tris (3-aminopropyl) amine, N,N-bis(2-amino ethyl)diethylene triamine, N"-bis (2-amino ethyl)-N-amino ethylpiperazine. Since these polyalkylene polyamine may be readily available industrially at low cost and the molecular weight thereof is relatively high, the hydroxyalkylated polyalkylene polyamine composition of the present invention having a plurality of hydroxyl groups may be conveniently manufactured at low cost.

In the method of present invention, specific examples of the N-alkylation method include a reduction methylation method in which the polyalkylene polyamine represented by the above general formula (4) is reacted with formaldehyde used as an N-alkylating agent in the presence of a hydrogenation catalyst under compressed hydrogen. If formaldehyde is used as an N-alkylating agent, not only the hydroxyalkylated polyalkylene polyamine composition of the present invention is obtained at low cost but also high catalytic property may be imparted to the composition.

According to the above-mentioned N-alkylation method, N-alkylated polyalkylene polyamines having a different number of added methyl groups may be obtained by varying the molar ratio of the polyalkylene polyamine represented by the above general formula (4) to formaldehyde. Then, if alkylene oxide such as 1,2-propylene oxide is added to the polyamines, the hydroxyalkylated polyalkylene polyamines represented by the above general formula (1) may be obtained.

Since the hydroxyalkylated polyalkylene polyamines obtained by the above method exist, after the reaction, as a mixture of a few different kinds in which the number of added methyl groups and the position thereof are varied and distillation thereof is difficult, it is substantially obtained as a composition including two of more kinds of hydroxyalkylated polyalkylene polyamine represented by the above general formula (1).

Although alkylene oxide is not particularly limited in the method of the present invention, examples thereof include ethylene oxide, 1,2-propylene oxide, and 1,2-butylene oxide.

Examples of the hydroxyalkylated polyalkylene polyamine composition of the present invention produced by the method of the present invention include, when diethylene triamine is used as the polyalkylene polyamine represented by the above general formula (4), compounds ranging from those in which four 1,2-propylene oxide are added to a monomethylated body to those in which two 1,2-propylene oxide are added to a trimethylated body, and specific examples thereof include, depending on the position of the methyl group, N-methyl N,N',N'',N''-tetrakis(2-hydroxypropyl)diethylene triamine, N'-methyl N,N,N'',N''-tetra(2-hydroxypropyl)diethylene triamine, N,N-dimethyl N',N'',N''-tris(2-hydroxypropyl)diethylene triamine, N,N'-dimethyl N,N'',N''-tris(2-hydroxypropyl)diethylene triamine, N,N,N'-trimethyl N'',N''-bis(2-hydroxypropyl)diethylene triamine, and N,N,N''-trimethyl N',N''-bis(2-hydroxypropyl)diethylene triamine, and these may be arbitrary combined to be a mixture. Also, the mixture may include, in an arbitrary ratio, by-products such as N,N,N',N'',N''-pentamethyldiethylene triamine, N,N,N'',N''-tetramethyl N'-(2-hydroxypropyl)diethylene triamine, N,N,N',N''-tetramethyl N''-(2-hydroxypropyl)diethylene triamine, and N,N,N',N'',N''-pentakis(2-hydroxypropyl)diethylene triamine.

Similarly, for the case where the polyalkylene polyamine represented by the above general formula (4) is a triethylene tetramine, examples thereof include compounds ranging from monomethylated bodies to tetramethylated bodies in which 1,2-propylene oxide is added to the position of active hydrogen of the compound. For the case where the polyalkylene polyamine represented by the above general formula (4) is a tetraethylene pentamine, examples thereof include compounds ranging from monomethylated bodies to pentamethylated bodies in which 1,2-propylene oxide is added to the position of the active hydrogen of the compound. For the case where the polyalkylene polyamine represented by the above general formula (4) is a pentaethylene hexamine, examples thereof include compounds ranging from monomethylated bodies to hexamethylated bodies in which 1,2-propylene oxide is added to the position of the active hydrogen of the compound. For the case where the polyalkylene polyamine represented by the above general formula (4) is a dipropylene triamine, examples thereof include compounds ranging from monomethylated bodies to tetramethylated bodies in which 1,2-propylene oxide is added to the position of the active hydrogen of the compound. For the case where the polyalkylene polyamine represented by the above general formula (4) is a dihexamethylene triamine, examples thereof include compounds ranging from monomethylated bodies to trimethylated bodies in which 1,2-propylene oxide is added to the position of the active hydrogen of the compound. For the case where the polyalkylene polyamine represented by the above general formula (4) is a tripropylene tetramine, examples thereof include compounds ranging from monomethylated bodies to tetramethylated bodies in which 1,2-propylene oxide is added to the position of the active hydrogen of the compound. For the case where the polyalkylene polyamine represented by the above general formula (4) is an N-aminoethyl piperazine, examples thereof include compounds of monomethylated bodies in which 1,2-propylene oxide is added to the position of the active hydrogen of the compound. For the case where the polyalkylene polyamine represented by the above general formula (4) is an N-2-(2'-aminoethyl) aminoethyl piperazine, examples thereof include compounds ranging from monomethylated bodies to dimethylated bodies in which 1,2-propylene oxide is added to the position of the active hydrogen of the compound. For the case where the polyalkylene polyamine represented by the above general formula (4) is an N,N'-bis(2-aminoethyl) piperazine, examples thereof include compounds ranging from monomethylated bodies to dimethylated bodies in which 1,2-propylene oxide is added to the position of the active hydrogen of the compound. For the case where the polyalkylene polyamine represented by the above general formula (4) is an N-2-(2'-(2''-aminoethyl)aminoethyl)aminoethyl piperazine, examples thereof include compounds ranging from monomethylated bodies to trimethylated bodies in which 1,2-propylene oxide is added to the position of the active hydrogen of the compound. For the case where the polyalkylene polyamine represented by the above general formula (4) is an N-2-(2'-aminoethyl)aminoethyl-N'-aminoethyl piperazine, examples thereof include compounds ranging from monomethylated bodies to trimethylated bodies in which 1,2-propylene oxide is added to the position of the active hydrogen of the compound. For the case where the polyalkylene polyamine represented by the above general formula (4) is an N,N'-bis(3-aminopropyl) piperazine, examples thereof include compounds ranging from monomethylated bodies to dimethylated bodies in which 1,2-propylene oxide is added to the position of the active hydrogen of the compound. For the case where the polyalkylene polyamine represented by the above general formula (4) is a tris(2-aminoethyl)amine, examples thereof include compounds ranging from monomethylated bodies to tetramethylated bodies in which 1,2-propylene oxide is added to the position of the active hydrogen of the compound. For the case where the polyalkylene polyamine represented by the above general formula (4) is a tris (3-aminopropyl)amine, examples thereof include compounds ranging from monomethylated bodies to tetramethylated bodies in which 1,2-propylene oxide is added to the position of the active hydrogen of the compound. For the case where the polyalkylene polyamine represented by the above general formula (4) is an N,N-bis(2-aminoethyl)diethylene triamine, examples thereof include compounds ranging from monomethylated bodies to tetramethylated bodies in which 1,2-propylene oxide is added to the position of the active hydrogen of the compound. These compounds may include by-products in an arbitrary ratio.

The hydroxyalkylated polyalkylene polyamine composition of the present invention is used as part of polyol or cross-linking agent in a method of producing polyurethane in which polyol and polyisocyanate are reacted in the presence of, as required by necessity, a blowing agent, a surfactant, a flame retardant, a cross-linking agent, a catalyst and/or the like.

The method of producing polyurethane according to the present invention is characterized by reacting polyol and polyisocyanate in the presence of the above-mentioned hydroxyalkylated polyalkylene polyamine composition of the present invention. Also, the method of producing polyurethane foam according to the present invention is characterized by further reacting the polyol and the isocyanate in the presence of a blowing agent in the above-mentioned method of producing polyurethane resin.

In the method of producing polyurethane resin according to the present invention, examples of other polyols used include conventionally known polyether polyol, polyester polyol, polymer polyol, and flame retardant polyol such as phosphorous containing polyol and halogen containing polyol. The polyol may be used alone or in a suitable mixture.

examples of the polyether polyol include those produced by using, as starting material, a compound having at least two active hydrogen groups, e.g., polyhydric alcohols such as ethyleneglycol, propyleneglycol, glycerin and trimethylol propane; amines such as ethylenediamine; and alkanol amines such as ethanol amine and diethanol amine, and carrying out an addition reaction with alkylene oxide such as ethylene oxide and propylene oxide (refer to, for example, Gunter Oertel, "Polyurethane Handbook", pp. 42-53 (1984 edition), Hanser Publishers (Germany).

Examples of the polyester polyol include those obtained by carrying out a dehydration condensation reaction of dibasic acid (mainly adipic acid) with glycol or triol, and those obtained by treating waste from nylon production, waste of trimethylol propane or pentaerythritol, and waste of phthalic acid type polyester, and deriving therefrom (refer to, for example, Keiji Iwata "Polyurethane Resin Handbook", page 117, (First Edition 1987) Nikkan Kogyou Shinbun, Ltd.).

Examples of the polymer polyol include polymerized polyol which is obtained by reacting the above-mentioned polyether polyol with ethylenic unsaturated monomer (for instance butadiene, acrylonitrile and styrene) in the presence of a radical polymerization catalyst.

Examples of the flame retardant polyol include phosphorous containing polyol obtained by adding alkyleneoxide to a phosphate compound, halogen containing polyol obtained by carrying out a ring-opening polymerization of epichlorohydrin or trichlorobutylene oxide, and phenol polyol.

Polyols having an average hydroxyl value of about 20 to 1000 mg KOH/g may be employed, and those having 20 to 100 mg KOH/g may be suitably used for a flexible polyurethane foam or a semi-rigid polyurethane foam product and those having 100 to 800 mg KOH/g may be suitably used for a spray type rigid polyurethane foam.

Examples of the polyisocyanate used in the method of producing polyurethane resin according to the present invention include aromatic polyisocyanate such as toluene diisocyanate (hereinafter may be referred to as TDI), diphenylmethane, diisocyanate (hereinafter referred to as MDI), naphthylene diisocyanate, and xylene diisocyanate; aliphatic polyisocyanate such as hexamethylene diisocyanate; cycloaliphatic polyisocyanate such as dicyclohexyl, diisocyanate and isophorone; and mixture thereof. Among these, TDI and derivatives thereof, and MDI and derivatives thereof are preferable, and these may be used in a mixture.

Examples of the TDI and derivatives thereof include a mixture of 2,4-TDI and 2,6-TDI, and terminal isocyanate prepolymer derivatives of TDI. Examples of the MDI and derivatives thereof include a mixture of MDI and its polymer of polyphenyl polymethylene diisocyanate, and/or diphenylmethane, diisocyanate derivative having a terminal isocyanate group.

Among these isocyanate, TDI and derivatives thereof, MDI and derivatives thereof, or mixture thereof may be suitably used for flexible polyurethane foam or semi-rigid polyurethane foam products, and a mixture of MDI and its polymer of polyphenyl polymethylene diisocyanate may be suitable used for a spray type rigid polyurethane foam.

Although the mixing ratio of polyisocyanate to polyol is not particularly limited, it is generally within a range of 60 to 400 in terms of isocyanate index (i.e., isocyanate group/active hydrogen group which may be reacted with the isocyanate group).

In the method of producing polyurethane resin according to the present invention, it is possible to use a catalyst as long as it does not deviate from the scope of the present invention. Examples of the catalyst include organometallic catalysts, carboxylic acid metallic salts, tertiary amines, and quaternary ammonium salts.

The organometallic catalyst is not particularly limited as long as it is conventionally known and is a metallic compound other than a lead, tin, or mercury containing type compound. Suitable examples thereof include bismuth octanoate, bismuth neodecanoate, zinc octanoate, zinc neodecanoate, zinc naphthenate, nickel octanoate, nickel naphthenate, and cobalt naphthenate. Since heavy metals such as lead, tin, and mercury cause toxic problems and environmental problems, the amount thereof used is preferably small.

Carboxylic acid metallic salts are not particularly limited and any conventionally known carboxylic acid may be used. Examples thereof include alkali metal salts or alkali earth metal salts of carboxylic acid. Carboxylic acid is not particularly limited and examples thereof include aliphatic mono- and di-carboxylic acids of acetic acid, propionic acid, 2-ethylhexanic acid, and adipic acid; aromatic mono- and di-carboxylic acids of benzoic acid, and phthalic acid. Also, suitable examples of metals which form carboxylic acid salt include alkali metals such as lithium, sodium, and potassium; and alkali earth metals such as calcium and magnesium.

Tertiary amines are not particularly limited and any conventionally known tertiary amines may be used. Examples of the tertiary amine compounds include N,N,N',N'-tetramethylethylene diamine, N,N,N',N'-tetramethylproylene diamine, N,N,N',N",N"-pentamethyldiethylene triamine, N,N,N',N", N"-pentamethyl-(3-aminopropyl)ethylene diamine, N,N,N', N",N"-pentamethyldipropylene triamine, N,N,N',N'-tetramethyl guanidine, 1,3,5-tris(N,N-dimethyl aminopropyl) hexahydro-S-triazine, 1,8-diazabicyclo[5.4.0]undecane-7 triethylene diamine, N,N,N',N'-tetramethyl hexamethylene diamine, N,N'-dimethylpiperazine, dimethyl cyclohexylamine, N-methylmorpholine, N-ethylmorpholine, bis(2-dimethylaminoethyl)ether, 1-methylimidazole, 1,2-dimethylimidazole, 1-isobutyl-2-methylimidazole, and 1-dimethylaminopropylimidazole.

Ammonium salts are not particularly limited and any known quaternary ammonium salts may be used. Examples thereof include halides of tetraalkyl ammonium such as tetramethyl ammonium chloride; hydroxides of tetraalkyl ammonium such as tetramethyl ammonium hydroxide salt;

and tetraalkyl ammonium organic salts such as tetramethyl ammonium2-ethylhexanate, 2-hydroxypropyl trimethyl ammonium formate, and 2-hydroxypropyl trimethyl ammonium2-ethylhexanoate.

In the method of producing polyurethane resin according to the present invention, the amount of catalyst used is generally 0.01 to 20 parts by weight, and preferably 0.05 to 10 parts by weight with respect to 100 parts by weight of polyol used. If the amount is 0.01 parts by weight or less, the curing rate of polyurethane resin decreases, and the moldability thereof is worsen. On the other hand, if the amount is more than 20 parts by weight, not only the effect of increasing the amount of catalyst is not obtained but also the moldability thereof may be worsen.

Specific examples of the blowing agent used in the method of producing polyurethane resin according to the present invention include freon type compounds, low-boiling hydrocarbons, water, and mixtures thereof. Examples of the freon type compounds include dichloromonofluoroethane (HCFC-141b), 1,1,1,3,3-pentafluoropropane (HFC-245fa), and 1,1,1,3,3-pentafluorobutane (HFC-365mfc). Among these, 1,1,1,3,3-pentafluoropropane (HFC-245fa), and 1,1,1,3,3-pentafluorobutane (HFC-365mfc) are preferable from the viewpoint of ozone layer destruction problem. As the low-boiling point hydrocarbons, hydrocarbons having a boiling point of 0 to 70° C. are generally used, and specific examples thereof include propane, butane, pentane, cyclopentane, hexane, and mixtures thereof. Among these blowing agents, water is especially preferable.

In the method of producing polyurethane resin according to the present invention, a surfactant may be used as a foam stabilizer if necessary. Examples of the surfactant used include conventionally known organic silicone type surfactants, and specific examples thereof include non-ionic surfactant such as organic siloxane-polyoxyalkylene copolymer and silicone-grease copolymer, and mixtures thereof. The amount thereof used is generally 0.1 to 10 parts by weight with respect to 100 parts by weight of polyol.

In the method of producing polyurethane resin according to the present invention, a cross-linking agent or a chain extending agent may be used if necessary. Examples of the cross-linking agent or chain extender include polyhydric alcohols of low molecular weight, such as ethylene glycol, 1,4-butanediol, and glycerin; amine polyols of low molecular weight such as diethanol amine and triethanol amine; and polyamines such as ethylenediamine, xylenediamine, and methylene bisorthochloroaniline.

In the method of producing polyurethane resin according to the present invention, a flame retardant may be used if necessary. Examples of the flame retardant include reactive flame retardants like phosphorous containing polyol such as propoxylated phosphorous and propoxylated dibuthylpyrophosphorous, which may be obtained by an addition reaction of phosphoric acid with alkylene oxide; tertiary phosphate such as tricresyl phosphate; halogen containing tertiary phosphate such as tris(2-chloroethyl) phosphate and tris(chloropropyl) phosphate; halogen containing organic compounds such as dibrompropanol, dibromoneopentyl glycol and tetrabromo bisphenol A; and inorganic compounds such as antimony oxide, calcium carbonate and aluminum phosphate. The amount of the flame retardant is not particularly limited and may be varied depending on the degree of flame resistance, however, it is generally 4 to 20 parts by weight with respect to 100 parts by weight of polyol.

In the method of producing polyurethane resin according to the present invention, colorants, antioxidants, and other conventionally known additives may be used in accordance with necessity. The type and amount of the additives may be in accord with the general use of the additives.

The method for producing polyurethane resin according to the present invention is carried out by rapidly mixing and stirring a mixture containing the above-mentioned raw materials, and then foam molding it by introducing into a suitable container or a mold. The mixing and stirring process may be carried out by using an ordinary mixer, or an exclusive polyurethane foaming machine. Examples of the polyurethane foaming machine include high pressure-, low pressure-, and spray type-machines.

Examples of polyurethane resin products include elastomer which does not use a blowing agent, and polyurethane foam which uses a blowing agent. Among these, production of polyurethane product is preferable, and examples of the polyurethane foam product include flexible, semi-rigid, and rigid products. Among these, soft car seat which is used as an automobile interior material, semi-rigid instrument panels and handles, and heat insulating building materials which are produced by a spray type rigid foam, are preferable.

Next, among the above-mentioned methods for producing polyurethane resin according to the present invention, the method for producing rigid polyurethane foam in which a certain reactive catalyst is used will be explained in detail. By using the above-mentioned hydroxyalkylated polyalkylene polyamine composition of the present invention together with a certain reactive catalyst, it becomes possible to manufacture rigid polyurethane foam, particularly spray-type rigid polyurethane foam which is molded by mixing and discharging polyurethane foam in a sprayed manner without using heavy metals.

The method for manufacturing rigid polyurethane foam according to the present invention is a method in which polyol is reacted with polyisocyanate in the presence of a blowing agent, a catalyst, and a foam stabilizer. In this method of producing rigid polyurethane foam, the hydroxyalkylated polyalkylene polyamine composition of the present invention is used as polyol, a tertiary amine compound which includes at least one active hydrogen group in its molecule is used as a catalyst, and one part by weight or more of water is used as a blowing agent with respect to 100 parts by weight of polyol.

In the method of manufacturing rigid polyurethane foam according to the present invention, the productivity increases as the amount of the hydroxyalkylated polyalkylene polyamine composition of the present invention used increases. However, from the viewpoint of reducing the cost for producing rigid polyurethane foam, it is preferable to use 0.01 to 20 parts by weight the polyamine composition with respect to 100 parts by weight of polyol used.

In the method of manufacturing rigid polyurethane foam according to the present invention, the hydroxyl value of the hydroxyalkylated polyalkylene polyamine composition of the present invention is generally 100 to 800 mg KOH/g, and preferably 200 to 700 mg KOH/g. If the hydroxyl value is less than 100 mg KOH/g, the degree of hardness of the rigid polyurethane foam obtained tends to be insufficient. If the hydroxyl value is greater than 800 mg KOH/g, the degree of mixing with polyisocyanate tends to be insufficient since the viscosity of the above-mentioned hydroxyalkylated polyalkylene polyamine becomes too large.

In the method of manufacturing rigid polyurethane foam according to the present invention, the amount of water used is generally one part by weight or more with respect to 100 parts by weight of polyol. If the amount of water is less than one part by weight, the density of rigid polyurethane products increases due to insufficient amount of carbon dioxide gas generated, and a larger amount of raw materials including polyol and polyisocyanate will be required.

In the method of manufacturing rigid polyurethane foam according to the present invention, the amount of the tertiary amine compound having at least one active hydrogen group in its molecule is generally 0.01 to 15 parts by weight with respect to 100 parts by weight of polyol. However, in order to improve work environment, it is preferable to use lesser amount thereof.

In the method of manufacturing rigid polyurethane foam according to the present invention, the tertiary amine compound having at least one active hydrogen group in its molecule is not particularly limited. However, from the viewpoint of odor thereof, use of N'-(2-hydroxyethyl)-N,N,N'-trimethyl bis(2-aminoethyl)ether, N,N-dimethylhexanol amine, N,N-dimethylaminoethoxy ethanol, N,N,N'-trimethyl-N'-(2-hydroxyethyl) ethylene diamine, N-(2-hydroxyethyl)-N,N',N", N"-tetramethyldiethylene triamine, N-(2-hydroxypropyl)-N, N',N",N"-tetramethyldiethylene triamine, N,N,N'-trimethyl-N'-(2-hydroxyethyl) propanediamine, N-methyl-N'-(2-hydroxyethyl) piperazine, bis(N,N-dimethylaminopropyl) amine, bis(N,N-dimethylaminopropyl) isopropanolamine, 2-amino quinuclidine, 3-amino quinuclidine, 4-amino quinuclidine, 2-quinuclidiol, 3-quinuclidinol, 4-quinuclidinol, 1-(2'-hydroxypropyl) imidazole, 1-(2'-hydroxypropyl)-2-methylimidazole, 1-(2'-hydroxyethyl) imidazole, 1-(2'-hydroxyethyl)-2-methylimidazole, 1-(2'-hydroxypropyl)-2-methylimidazole, 1-(3'-aminopropyl) imidazole, 1-(3'-aminopropyl)-2-methylimidazole, 1-(3'-hydroxypropyl) imidazole, 1-(3'-hydroxypropyl)-2-methylimidazole, N,N-dimethylaminopropyl-N'-(2-hydroxyethyl)amine, N,N-dimethylaminopropyl-N',N'-bis(2-hydroxyethyl)amine, N,N-dimethylaminopropyl-N',N'-bis(2-hydroxypropyl)amine, N,N-dimethylaminoethyl-N',N'-bis(2-hydroxyethyl)amine, N,N-dimethylaminoethyl-N'N'-bis(2-hydroxypropyl)amine, and so forth are preferable.

Also, in the method of manufacturing rigid polyurethane foam according to the present invention, from the viewpoints of availability of raw materials and catalytic activity, N'-(2-hydroxyethyl)-N,N,N'-trimethyl bis(2-aminoethyl)ether, N,N-dimethylaminoethoxy ethanol, N,N,N'-trimethyl-N'-(2-hydroxyethyl)ethylene diamine, N-(2-hydroxyethyl)-N, N'N",N"-tetramethyldiethylene triamine, N-(2-hydroxypropyl)-N,N',N",N"-amine, and bis(N,N-dimethylaminopropyl) isopropanolamine are more preferable as the tertiary amine compound having at least one active hydrogen group in its molecule.

In the method of manufacturing rigid polyurethane foam according to the present invention, from the viewpoints of availability of raw materials and catalytic activity, N'-(2-hydroxyethyl)-N,N,N'-trimethyl bis(2-aminoethyl)ether, N,N-dimethylaminoethoxy ethanol, N,N,N'-trimethyl-N'-(2-hydroxyethyl)ethylene diamine, N-(2-hydroxyethyl)-N, N',N", N"-tetramethyldiethylene triamine, N-(2-hydroxypropyl)-N, N',N",N"-amine, and bis(N,N-dimethylaminopropyl) isopropanolamine are more preferable as the tertiary amine compound having at least one active hydrogen group in its molecule.

Examples of polyols other than the hydroxyalkylated polyalkylene polyamine composition of the present invention used in the method of manufacturing rigid polyurethane foam of the present invention include the above-mentioned conventionally known polyether polyol, polyester polyol, polymer polyol, and flame retardant polyol such as phosphorous containing polyol and halogen containing polyol. These polyols may be used together in a suitable mixture thereof.

In the method of manufacturing rigid polyurethane foam according to the present invention, polyol having an average hydroxyl value of about 20 to 1000 mg KOH/g may be used. As for the spray type rigid polyurethane foam, those having 100 to 800 mg KOH/g may be suitably used.

Examples of the polyisocyanate may be used in the method of manufacturing rigid polyurethane foam according to the present invention include aromatic polyisocyanate such as TDI, MDI, naphthylene diisocyanate, and xylene diisocyanate. Among these, MDI and derivatives thereof are preferable, and these may be used in a mixture.

Examples of the TDI and derivatives thereof include a mixture of 2,4-TDI and 2,6-TDI, and terminal isocyanate prepolymer derivatives of TDI. Examples of the MDI and derivatives thereof include a mixture of MDI and its polymer of polyphenyl polymethylene diisocyanate, and/or diphenylmethane diisocyanate derivative having a terminal isocyanate group.

Although the mixing ratio of polyisocyanate to polyol is not particularly limited, it is generally within a range of 60 to 400 in terms of isocyanate index (i.e., isocyanate group/active hydrogen group which may be reacted with the isocyanate group).

In the method of producing rigid polyurethane foam according to the present invention, it is possible to use catalyst, other than the tertiary amine compound having at least one active hydrogen group in its molecule, as long as it does not deviate from the scope of the present invention. Examples of such catalyst include the above-mentioned organometallic catalyst, carboxylic acid metallic salts, tertiary amines, and quaternary ammonium salts.

Although water is used as the blowing agent in the method of producing polyurethane foam according to the present invention, other blowing agents such as the above-mentioned freon type compounds, low-boiling point hydrocarbons, and carbon dioxide gas, etc., may be used together with water.

In the method of producing rigid polyurethane foam according to the present invention, it is possible to use the above-mentioned surfactant as a foam stabilizer if necessary. The amount thereof used is generally 0.1 to 10 parts by weight with respect to 100 parts by weight of polyol.

In the method of producing rigid polyurethane foam according to the present invention, it is possible to use the above-mentioned cross-linking agent or the chain extender if necessary.

In the method of producing rigid polyurethane foam according to the present invention, it is possible to use the above-mentioned flame retardant if necessary. The amount of flame retardant may vary depending on the required degree of flame resistance and not particularly limited. However, it is generally in the range of 4 to 20 parts by weight with respect to 100 parts of polyol.

In the method of producing rigid polyurethane foam according to the present invention, colorants, antioxidants, and other conventionally known additives may be used in accordance with necessity. The type and amount of the additives may be in accord with the general use of the additives.

Examples of the method for producing rigid polyurethane foam according to the present invention include, specifically, a method in which a mixture containing the above-mentioned raw materials are rapidly mixed and stirred, and then it is introduced into a suitable container to be subjected to a foam molding process, and a method in which heat insulating building materials are produced by using a spray type device. The mixing and stirring processes may be carrying out by using an ordinary mixer, or an exclusive polyurethane foaming machine. Examples of the polyurethane foaming machine include high pressure-, low pressure-, and spray type-machines.

As examples of rigid polyurethane foam products manufactured by the method of the present invention, heat insulating building materials manufactured by spray type rigid polyurethane foam whose problem of odor needs to be solved in particular, are preferable.

EXAMPLES

Hereinafter, the present invention will be described based on the examples, however, the present invention is not limited to these examples by any means.

In the following, the hydroxyl value of each hydroxyalkylated polyalkylene polyamines was measured in accordance with JIS-K-1557-1970 (i.e., a so-called phthalic anhydride method). The hydroxyl value (mg KOH/g) means an amount of KOH (mg) required for saponifying 1 g of alcohols by using KOH.

Polyhydric alcohols which are obtained by adding alkylene oxide to raw material compounds take a form of mixture of a plurality of compounds having a large distribution in their molecular weights, as can be seen in the present invention. Since the isolation and identification of the compounds are difficult, a method was adopted in which the hydroxyl value was measured and the number of hydroxyl groups per average molecular weight of the product was calculated. As described above, the hydroxyl value (mg KOH/g) is defined as the following equation:

Hydroxyl value=No. of OH groups in a molecule/average molecular weight×56.11×1000

Example 1

150 g (1.45 mols) of diethylenetriamine (DETA manufactured to Tosoh Corporation), 150 g of water, and 0.5 g of Pd—C catalyst (5% support) were charged to a 1000 ml autoclave with a stirrer. After sealing the autoclave and carrying out hydrogen substitution, the temperature of the autoclave was increased to 120° C. while stirring. Then, while introducing hydrogen at a pressure of 3 MPa in the autoclave, 295 g (3.63 mols) of a 37% aqueous formalin solution was supplied by a pump to the autoclave over 4 hours. After an aging reaction was carried out for 1 hour, the reaction mixture was cooled and removed.

After evaporating water from the reaction solution using a distillation apparatus, an N-methylated diethylenetriamine, which is the product, was distilled under reduced pressure to obtain 159 g thereof. From gas chromatography analysis and $^1$H-NMR analysis, it was determined that 53% of the hydrogen groups bonded to nitrogen atoms on the diethylenetriamine had converted to methyl groups (in other words, in the above-mentioned general formula (3), among $R_1$ to $R_5$, the ratio of $C_1$ to $C_3$ alkyl groups to hydrogen atoms is [$C_1$ to $C_3$ alkyl groups]/[hydrogen atoms]=53/47 (molar ratio)), and it was determined by gas chromatography that the composition was 14% monomethyl compounds, 33% dimethyl compounds, 36% trimethyl compounds, and 17% tetramethyl compounds. This amine compound was used as compound A.

70.2 g of compound A was charged to the autoclave. After sealing the autoclave and carrying out nitrogen substitution, the temperature of the autoclave was increased to 120° C. while stirring. Then, 71.7 g of 1,2-propylene oxide was supplied by pump over 4 hours. After an aging reaction was carried out for 1 hour, the reaction solution was cooled and removed. Then, evaporation was carried out under the conditions of 60° C./20 mmHg for 2 hours, and 136 g of hydroxyalkylated polyalkylene polyamine composition 1 (hereinafter may be referred to as polyol 1) was obtained. The hydroxyl value thereof was 465 mg KOH/g. Thus, the average molecular weight of the hydroxyalkylated polyalkylene polyamine composition 1 is presumed to be 284.

Example 2

77.2 g of compound A was charged to the autoclave. After sealing the autoclave and carrying out nitrogen substitution, the temperature of the autoclave was increased to 80° C. while stirring. Then, 62.6 g of ethylene oxide was supplied in steps from a pressure-resistant container by a pump over 4 hours. After an aging reaction was carried out for 1 hour at 100° C., the reaction solution was cooled and removed. Then, evaporation was carried out under the conditions of 60° C./20 mmHg for 2 hours, and 134 g of hydroxyalkylated polyalkylene polyamine composition 2 was obtained. The hydroxyl value thereof was 529 mg KOH/g. Thus, the average molecular weight of the hydroxyalkylated polyalkylene polyamine composition 2 is presumed to be 249.

Example 3

The reaction and distillation were carried out under the same conditions as in Example 1 except that the amount of the 37% aqueous formalin solution was changed to 470 g (5.80 mols), and 182 g of N-methylated diethylenetriamines was obtained. By the same analyses as in Example 1, it was determined that 79% of the hydrogen groups bonded to nitrogen atoms in the diethylenetriamine had converted to methyl groups (in other words, in the above-mentioned general formula (3), among $R_1$ to $R_5$, the ratio of $C_1$ to $C_3$ alkyl groups to hydrogen atoms is [$C_1$ to $C_3$ alkyl groups]/[hydrogen atoms]=79/21 (molar ratio)) and that the composition was 4% dimethyl compounds, 19% trimethyl compounds, 52% tetramethyl compounds, and 25% pentamethyl compounds. This amine compound was used as compound B.

111 g of compound B was charged to the autoclave. After sealing the autoclave and carrying out nitrogen substitution, the temperature of the autoclave was increased to 120° C. while stirring. Then, 45 g of 1,2-propylene oxide was supplied by a pump over 4 hours. After an aging reaction was carried out for 1 hour, the reaction solution was cooled and removed. Then, evaporation was carried out under the conditions of 60° C./20 mmHg for 2 hours, and 151 g of hydroxyalkylated polyalkylene polyamine composition 3 was obtained. The hydroxyl value thereof was 265 mg KOH/g. Thus, the average molecular weight of the hydroxyalkylated polyalkylene polyamine composition 3 is presumed to be 222.

Example 4

111 g of compound B was charged to a 200 ml autoclave provided with a stirrer. After sealing the autoclave and carrying out nitrogen substitution, the temperature of the autoclave was increased to 80° C. while stirring. Then, 36 g of ethylene oxide was supplied in steps from a pressure-resistant container by a pump over 4 hours. After an aging reaction was carried out for 1 hour, the reaction solution was cooled and removed. Then, evaporation was carried out under the conditions of 60° C./20 mmHg for 2 hours, and 140 g of hydroxyalkylated polyalkylene polyamine composition 4 was obtained. The hydroxyl value thereof was 284 mg KOH/g.

Thus, the average molecular weight of the hydroxyalkylated polyalkylene polyamine composition 4 is presumed to be 207.

Example 5

375 g of tetraethylenepentamine which includes branched chains and annular rings in addition to linear chains (TEPA manufactured by Tosoh Corporation), and 1.3 g of Pd—C catalyst (5% support) were charged to a 1000 ml autoclave with a stirrer. After sealing the autoclave and carrying out hydrogen substitution, the temperature of the autoclave was increased to 120° C. while stirring. Then, while introducing hydrogen at a pressure of 3 MPa in the autoclave, 480 g of a 37% aqueous formalin solution was supplied by a pump to the autoclave over 9 hours. After an aging reaction was carried out for 1 hour, the reaction mixture was cooled and removed.

After evaporating water from the reaction solution using a distillation apparatus, 335 g of an N-methylated tetraethylenepentamine, which is the product, was obtained under reduced pressure. From the same analysis performed in Example 1 on this product, it was determined that 52% of the hydrogen groups bonded to nitrogen atoms on the tetraethylenepentamine had converted to methyl groups (in other words, in the above-mentioned general formula (3), among $R_1$ to $R_5$, the ratio of $C_1$ to $C_3$ alkyl groups to hydrogen atoms is [$C_1$ to $C_3$ alkyl groups]/[hydrogen atoms]=52/48 (molar ratio)), and it was determined that the composition was mainly composed of trimethyl compounds and tetramethyl compounds. However, detailed constitution of the composition could not be determined. This amine compound was used as compound C.

97.7 g of compound C was charged to the autoclave. After sealing the autoclave and carrying out nitrogen substitution, the temperature of the autoclave was increased to 80° C. while stirring. Then, 58 g of ethylene oxide was supplied in steps from a pressure-resistant container by pump over 4 hours. After an aging reaction was carried out for 1 hour at 100° C., the reaction solution was cooled and removed. Then, evaporation was carried out under the conditions of 60° C./20 mmHg for 2 hours, and 150 g of hydroxyalkylated polyalkylene polyamine composition 5 was obtained. The hydroxyl value thereof was 439 mg KOH/g.

Example 6

97.7 g of compound C was charged to a 200 ml autoclave provided with a stirrer. After sealing the autoclave and carrying out nitrogen substitution, the temperature of the autoclave was increased to 120° C. while stirring. Then, 74 g of 1,2-propylene oxide was supplied by a pump over 4 hours. After an aging reaction was carried out for 1 hour, the reaction solution was cooled and removed. Then, evaporation was carried out under the conditions of 60° C./20 mmHg for 2 hours, and 166 g of hydroxyalkylated polyalkylene polyamine composition 6 (hereinafter may be referred to as polyol 6) was obtained. The hydroxyl value thereof was 395 mg KOH/g.

Example 7

80.1 g of compound C was charged to a 200 ml autoclave provided with a stirrer. After sealing the autoclave and carrying out nitrogen substitution, the temperature of the autoclave was increased to 120° C. while stirring. Then, 79 g of 1,2-propylene oxide was supplied by a pump over 4 hours. After an aging reaction was carried out for 1 hour, the reaction solution was cooled and removed. Then, evaporation was carried out under the conditions of 60° C./20 mmHg for 2 hours, and 150 g of hydroxyalkylated polyalkylene polyamine composition 7 (hereinafter may be referred to as polyol 7) was obtained. The hydroxyl value thereof was 376 mg KOH/g.

Example 8

150 g (1.14 moles, reagent) of dipropylenetriamine, and 0.5 g of Pd—C catalyst (5% support) were charged to a 500 ml autoclave with a stirrer. After sealing the autoclave and carrying out hydrogen substitution, the temperature of the autoclave was increased to 120° C. while stirring. Then, while introducing hydrogen at a pressure of 3 MPa in the autoclave, 232 g of a 37% aqueous formalin solution was supplied by a pump to the autoclave over 4 hours. After an aging reaction was carried out for 1 hour, the reaction mixture was cooled and removed.

After evaporating water from the reaction solution using a distillation apparatus, distillation was carried out under reduced pressure and 142 g of an N-methylated dipropylenetriamine, which is the product, was obtained. From the same analysis performed in Example 1 on this product, it was determined that 51% of the hydrogen groups bonded to nitrogen atoms on the dipropylenetriamine had converted to methyl groups (in other words, in the above-mentioned general formula (3), among $R_1$ to $R_5$, the ratio of $C_1$ to $C_3$ alkyl groups to hydrogen atoms is [$C_1$ to $C_3$ alkyl groups]/[hydrogen atoms]=51/49 (molar ratio)), and it was determined that the composition was 13% monomethyl compounds, 36% dimethyl compounds, 38% trimethyl compounds, and 13% tetramethyl compounds. This amine compound was used as compound C.

90.5 g of compound D was charged to an autoclave provided with a stirrer. After sealing the autoclave and carrying out nitrogen substitution, the temperature of the autoclave was increased to 120° C. while stirring. Then, 75 g of 1,2-propylene oxide was supplied by pump over 4 hours. After an aging reaction was carried out for 1 hour, the reaction solution was cooled and removed. Then, evaporation was carried out under the conditions of 60° C./20 mmHg for 2 hours, and 160 g of hydroxyalkylated polyalkylene polyamine composition 8 (hereinafter may be referred to as polyol 8) was obtained. The hydroxyl value thereof was 420 mg KOH/g.

Example 9

83.7 g of compound D was charged to a 200 ml autoclave provided with a stirrer. After sealing the autoclave and carrying out nitrogen substitution, the temperature of the autoclave was increased to 80° C. while stirring. Then, 59 g of ethylene oxide was supplied in steps from a pressure-resistant container by a pump over 4 hours. After an aging reaction was carried out for 1 hour at 100° C., the reaction solution was cooled and removed. Then, evaporation was carried out under the conditions of 60° C./20 mmHg for 2 hours, and 137 g of hydroxyalkylated polyalkylene polyamine composition 9 was obtained. The hydroxyl value thereof was 490 mg KOH/g.

Example 10

75.3 g of compound D was charged to a 200 ml autoclave provided with a stirrer. After sealing the autoclave and carrying out nitrogen substitution, the temperature of the autoclave was increased to 120° C. while stirring. Then, 84 g of 1,2- buthylene oxide was supplied by a pump over 4 hours. After an aging reaction was carried out for 1 hour, the reaction solution was cooled and removed. Then, evaporation was carried out under the conditions of 60° C./20 mmHg for 2 hours, and 151 g of hydroxyalkylated polyalkylene polyamine composition 10 was obtained. The hydroxyl value thereof was 400 mg KOH/g.

Example 11

The reaction and distillation were carried out under the same conditions as in Example 5 except that the amount of the 37% aqueous formalin solution was changed to 269 g (3.32 mols), and 147 g of N-methylated tetraethylenepentamines were obtained. By the same analyses, it was determined that 71% of the hydrogen groups bonded to nitrogen atoms in the tetraethylenepentamine had converted to methyl groups and that the main constituent was pentamethyls. However, detailed constitution of the composition could not be determined. This amine compound was used as compound E.

104.4 g of compound E was charged to a 200 ml autoclave provided with a stirrer. After sealing the autoclave and carrying out nitrogen substitution, the temperature of the autoclave was increased to 120° C. while stirring. Then, 45 g of 1,2-propylene oxide was supplied by a pump over 4 hours. After an aging reaction was carried out for 1 hour, the reaction solution was cooled and removed. Then, evaporation was carried out under the conditions of 60° C./20 mmHg for 2 hours, and 147 g of hydroxyalkylated polyalkylene polyamine composition 11 was obtained. The hydroxyl value thereof was 275 mg KOH/g.

Example 12

104.4 g of compound E was charged to a 200 ml autoclave provided with a stirrer. After sealing the autoclave and carrying out nitrogen substitution, the temperature of the autoclave was increased to 80° C. while stirring. Then, 35 g of ethylene oxide was supplied in steps from a pressure resistant container by a pump over 4 hours. After an aging reaction was carried out for 1 hour at 100° C., the reaction solution was cooled and removed. Then, evaporation was carried out under the conditions of 60° C./20 mmHg for 2 hours, and 134 g of hydroxyalkylated polyalkylene polyamine composition 12 was obtained. The hydroxyl value thereof was 296 mg KOH/g.

Example 13

The reaction and distillation were carried out under the same conditions as in Example 5 except that the amount of the 37% aqueous formalin solution was changed to 115 g (1.42 mols), and 125 g of N-methylated tetraethylenepentamines were obtained. As a result of analyses, it was found that 30% of the hydrogen groups bonded to nitrogen atoms in the tetraethylenepentamine had converted to methyl groups and that the main constituent was dimethyls. However, detailed constitution of the composition could not be determined. This amine compound was used as compound F.

71.7 g of compound F was charged to an autoclave. After sealing the autoclave and carrying out nitrogen substitution, the temperature of the autoclave was increased to 120° C. while stirring. Then, 85.4 g of 1,2-propylene oxide was supplied by a pump over 4 hours. After an aging reaction was carried out for 1 hour, the reaction solution was cooled and removed. Then, evaporation was carried out under the conditions of 60° C./20 mmHg for 2 hours, and 152 g of hydroxy-alkylated polyalkylene polyamine composition 13 was obtained. The hydroxyl value thereof was 500 mg KOH/g.

Example 14

71.7 g of compound E was charged to an autoclave. After sealing the autoclave and carrying out nitrogen substitution, the temperature of the autoclave was increased to 80° C. while stirring. Then, 68 g of ethylene oxide was supplied in steps from a pressure resistant container by a pump over 4 hours. After an aging reaction was carried out for 1 hour at 100° C., the reaction solution was cooled and removed. Then, evaporation was carried out under the conditions of 60° C./20 mmHg for 2 hours, and 134 g of hydroxyalkylated polyalkylene polyamine composition 14 was obtained. The hydroxyl value thereof was 576 mg KOH/g.

Examples 15 to 18 and Comparative Examples 1 to 4

In the following Examples, semi-rigid polyurethane foam was produced by using the hydroxyalkylated polyalkylene polyamine composition of the present invention, and in the Comparative Examples, semi-rigid polyurethane foam was produced by using various catalysts instead of the hydroxyalkylated polyalkylene polyamine composition of the present invention.

Premix A was prepared by using the amount of raw materials shown in Table 1. The amount of triethanol amine was adjusted in accordance with the amount of each hydroxyalkylated polyalkylene polyamine added so that the cross-linking density of the polymer became the same.

TABLE 1

| | Parts by Weight (pbw) |
|---|---|
| Polyol A [1] | 100 |
| Triethanol amine | Varies |
| Water | 2.8 |
| Catalyst | Varies |
| Hydroxyalkylated polyalkylene polyamine | Varies |
| Isocyanate [2] | INDEX 105 [3] |

[1] FA-703, polyether polyol manufactured by Sanyo Chemical Industries, Ltd.
[2] Isocyanate (MDI): MR-200 (Nippon Polyurethane Industry Co., Ltd)
[3] INDEX = (No. of moles of NCO groups/No. of moles of OH groups) × 100

105.8 g of Premix A was placed in a 300 ml of polyethylene cup, and the hydroxyalkylated polyalkylene polyamine of the present invention of catalyst shown in Table 2 was added in an amount which made the reactivity thereof to be 50 seconds in terms of gelling time, and the temperature was adjusted to be 25° C. An isocyanate solution, the temperature of which was adjusted to be 25° C. in a separate container was added to the cup of Premix A in an amount which made the isocyanate Index (=isocyanate groups/OH groups (molar ratio)×100) to be 105, and rapidly stirred at 3000 rpm for 5 seconds by using an agitating device. The temperature of the mixed solution obtained by mixing and stirring was transferred to a 2 L polyethylene cup, the temperature of which had been adjusted to 40° C., and the reactivity during foaming was measured.

Then, the mixed solution was placed in a mold (made of aluminum, inner size: 295×305×25 mm), the temperature of which was adjusted to be 40° C., so that the total foam density became 94 kg/m$^3$ by the same procedure, and the cover was closed to perform foam molding. Three minutes after starting mixing, foam was removed and after one minute, the hardness of the foam at demolding was measured. Also, the foam hardness and odor of the foam were measured from the molded foam and compared. Results are shown in Table 2. Note that the measuring method of each item was as follows.

(1) Measured Items for Reactivity

Cream time: start time of foaming and start time of rising foam were visually measured.

○: no discoloration
Δ: discolored to red

Since the color of polyvinyl chloride sheet changes to red due to amine discharged from the foam, the discoloration of sheet indicates a discharge of amine from the foam, and no discoloration indicates little discharge of amine.

TABLE 2

|  | Ex. 15 | Ex. 16 | Ex. 17 | Ex. 18 | C. Ex 1 | C. Ex 2 | C. Ex 3 | C. Ex 4 |
|---|---|---|---|---|---|---|---|---|
| Amount add (pbw) | | | | | | | | |
| TEOA [1] | 2.3 | 2.4 | 2.4 | 2.3 | 3 | 3 | 3 | 3 |
| Polyol 1 | 1.8 | | | | | | | |
| Polyol 6 | | 1.8 | | | | | | |
| Polyol 7 | | | 1.9 | | | | | |
| Polyol 8 | | | | 2.1 | | | | |
| L33 [2] | | | | | 1 | | | |
| DMAPA [3] | | | | | | 1 | | |
| TEPAPM [4] | | | | | | | 0.6 | |
| Monool [5] | | | | | | | | 0.8 |
| Reactivity (sec) | | | | | | | | |
| Cream Time | 15 | 16 | 16 | 17 | 20 | 15 | 11 | 13 |
| Gelling Time | 50 | 50 | 50 | 50 | 50 | 50 | 50 | 51 |
| Rise Time | 65 | 66 | 66 | 69 | 67 | 66 | 64 | 67 |
| Foam Properties | | | | | | | | |
| Total Density (kg/m$^3$) | 94 | 94 | 94 | 94 | 94 | 94 | 94 | 94 |
| Hardness at demolding (Shore C) | 12 | 17 | 19 | 18 | 3 | 0 | 12 | 7 |
| Foam hardness (Shore C) | 30 | 30 | 32 | 32 | 32 | 23 | 31 | 24 |
| VOCs | | | | | | | | |
| Odor at work environment | ○ | ○ | ○ | ○ | Δ | X | Δ | Δ |
| PVC discoloration | ○ | ○ | ○ | ○ | X | ○ | X | ○ |

[1] Triethanol amine (product of Kanto Chemical Co., Ltd.)
[2] Triethylene diamine 33.3% dipropylene glycol solution ("TEDA-L33", a product of Tosoh Corporation)
[3] N,N-dimethylpropane diamine (reagent)
[4] 100% methylated tetraethylenepentamine including branched chains and annular rings in addition to linear chains ("TEPA" a product of Tosoh Corporation)
[5] N-(2-hydroxypropyl-N,N',N",N"-tetramethyldiethylene triamine (synthetic composition)

Gelling time: time required to change from a liquid-like substance to a resin-like substance by the reaction was visually measured.

Rise time: time when the rising of foam stopped was visually measured.

(2) Odor During Operation

Three monitoring persons were stood one meter behind a worker who carried out a preparation of reaction liquid and evaluated the odor recognized during the operation as follows.

○: little unpleasant odor
Δ: a little unpleasant odor
x: significant unpleasant odor (3) Hardness of Foam at Demolding Three minutes after starting mixing, the foam was removed, and after one minute, the hardness of foam at demoling was measured by using a Shore C sclerosope.

(4) Hardness of Foam

Three minutes after starting mixing, the foam was removed, and after 24 hours, the hardness of foam was measured by using a Shore C sclerosope.

(5) Polyvinyl Chloride Sheet Staining Test (PVC Discoloration)

Foam including skin was cut into a piece of 7×7×2.5 cm, and this was placed into a 2000 ml separable flask. A piece of 5×5 cm white polyvinyl chloride sheet was hung therein and the cover was closed to seal the flask. After leaving at 100° C. for 72 hours, the degree of stain of polyvinyl chloride sheet was visually confirmed and the change of color thereof was evaluated as follows.

As is obvious from the above Table, Examples 15 to 18 in which the hydroxyalkylated polyalkylene polyamine composition of the present invention was used, the hardness at demoling of the polyurethane foam obtained is high. Also, there was little odor at work environment, and no stain of polyvinyl chloride was observed.

On the other hand, in Comparative Example 1 in which a general tertiary amine catalyst was used, the hardness at demoling was low. Also, there was a little odor in work environment, and the polyvinyl chloride sheet was stained. In Comparative Example 2 in which a reactive tertiary amine catalyst was used, the hardness at demoling and the hardness of foam were low, and there was significant odor in work environment. In Comparative Example 3 in which a compound whose active hydrogen groups of polyalkylene polyamine had been substituted by methyl groups was used, there was a little odor in work environment, and the polyvinyl chloride sheet was stained. In Comparative Example 4 in which a compound whose one of active hydrogen groups had been oxyalkylated using 1,2-propylene oxide and other active hydrogen groups had been substituted by methyl groups, the hardness at demoling and the hardness of the foam were low, and there was a little odor in work environment.

Examples 19 to 22 and Comparative Examples 5 to 7

In the following Examples, flexible polyurethane foam was produced by using the hydroxyalkylated polyalkylene polyamine composition of the present invention, and in the Comparative Examples, flexible polyurethane foam was produced by using various catalysts instead of the hydroxyalkylated polyalkylene polyamine composition of the present invention.

Premix B was prepared by using the amount of raw materials shown in Table 3.

TABLE 3

|  | Parts by Weight (pbw) |
|---|---|
| Polyol B [1] | 92.6 |
| Polyol C [2] | 1.9 |
| Cross-linking agent B [3] | 0.65 |
| Water | 3.2 |
| Foam stabilizer [4] | 1.0 |
| Isocyante [5] | INDEX = 100 [6] |

[1] CP4711, polyether polyol manufactured by Dow Chemical Company
[2] CP1421, polyether polyol manufactured by Dow Chemical Company
[3] Diethanol amine (product of Kanto Chemical Co., Ltd.)
[4] B4113LF (silicone surfactant, product of Goldschmied Co.)
[5] NE112, isocyanate manufactured by Dow Chemical Company
[6] INDEX = (No. of moles of NCO groups/No. of moles of OH groups) × 100

After 100.4 g of Premix B was placed in a 300 ml of polyethylene cup, the hydroxyalkylated polyalkylene polyamine of the present invention or catalyst shown in Table 4 was added, and the temperature was adjusted to be 20° C. 56.2 g of an isocyanate solution, the temperature of which was adjusted to be 20° C. in a separate container, which makes the isocyanate Index (=isocyanate groups/OH groups (molar ratio)×100) to be 100 was added to the cup of Premix B, and rapidly stirred at 6000 rpm for 5 seconds by using an agitating device. The temperature of the mixed solution obtained by mixing and stirring was transferred to a 2 L polyethylene cup, the temperature of which had been adjusted to 40° C., and the reactivity during foaming was measured.

Then, the mixed solution was introduced into a mold (made of aluminum, inner size: 250×250×80 mm), the temperature of which was adjusted to be 60° C., from an edge portion thereof, and the cover was closed to perform foam molding. Three minutes after starting mixing, foam was removed. Results are shown in Table 4. Note that the measuring method of each item was as follows.

(1) Measured Items for Reactivity

Cream time: start time of foaming and start time of rising foam were visually measured.

Gelling time: time required to change from a liquid-like substance to a resin-like substance by the reaction was visually measured.

Rise time: time when the rising of foam stopped was visually measured.

(2) Odor During Operation

Three monitoring persons were stood one meter behind a worker who carried out a preparation of reaction liquid and evaluated the odor discharged during the operation as follows.

○: little unpleasant odor
Δ: a little unpleasant odor
x: significant unpleasant odor (3) Hardness of Foam Three minutes after starting mixing, the foam was removed. Immediately after that, the foam was force-compressed so as to achieve cell communication, and a 65% compressed strength was measured in accordance with JIS-K6401-1997 after 24 hours.

(4) Amine Odor of Foam

Foam to which foam core density was measured was cut into a piece of 5×5×5 cm, and the piece was placed in a mayonnaise container and cover was closed. After heating at 50° C. for one day, the smell of the piece was monitored by 10 persons and the strength or amine odor thereof was evaluated.

○: little odor
Δ: a little odor
x: strong ordor

TABLE 4

|  | Ex. 19 | Ex. 20 | Ex. 21 | Ex. 22 | C. Ex 5 | C. Ex 6 | C. Ex 7 |
|---|---|---|---|---|---|---|---|
| Amount add (pbw) | | | | | | | |
| L33 [1] | | | 0.75 | 0.75 | | 1.5 | 0.75 |
| DMEA [2] | | | | | 2.8 | | 1.2 |
| Polyol 7 | 3.6 | | 1.4 | | | | |
| Polyol 8 | | 4.2 | | 1.8 | | | |
| Reactivity (sec) | | | | | | | |
| Cream Time | 8 | 8 | 8 | 8 | 7 | 8 | 7 |
| Gelling Time | 43 | 42 | 42 | 43 | 43 | 44 | 43 |
| Rise Time | 48 | 53 | 60 | 57 | 56 | 61 | 58 |
| Foam Properties | | | | | | | |
| Total Density (kg/m$^3$) | 52 | 52 | 52 | 52 | 52 | 52 | 52 |
| Mold core density (kg/m$^3$) | 51 | 50 | 49 | 49 | 50 | 49 | 50 |
| Hardness ILD 65% (kg/m$^3$) | 20 | 21 | 21.8 | 20.7 | 17.7 | 20.8 | 18.6 |
| VOCs | | | | | | | |
| Odor at work environment | ○ | ○ | Δ | Δ | X | X | X |
| Amine odor of foam | ○ | ○ | Δ | Δ | Δ | X | X |

[1] Triethylene diamine 33.3% diproplylene glycol solution ("TEDA-L33", a product of Tosoh Corporation)
[2] N,N-dimethyl ethanol amine (product of Kanto Chemical Co., Ltd.)

As is obvious from the above Table, Examples 19 and 20 in which the hydroxyalkylated polyalkylene polyamine composition of the present invention was used, the polyurethane foam obtained had a sufficient hardness and there was little odor at the work environment as well as from the foam. In Examples 21 and 22 in which the hydroxyalkylated polyalkylene polyamine composition of the present invention was used and the amount of general tertiary amine catalyst used was reduced by half, the polyurethane foam obtained had a sufficient hardness and there was a little odor at the work environment and from the foam.

On the other hand, in Comparative Example 5 in which a general reactive catalyst was used, the hardness of obtained polyurethane foam was insufficient and there was significant odor in work environment. In Comparative Example 6 in which a general tertiary amine catalyst was used, there was significant odor in work environment as well as from the foam. In Comparative Example 7 in which a general reactive catalyst was used in combination with a general tertiary amine catalyst, the hardness of obtained polyurethane foam was insufficient and there was significant odor in work environment and from the foam.

Examples 23 to 25 and Comparative Examples 8 to 11

In the following Examples 23 and 24, rigid polyurethane foam was produced by using the hydroxyalkylated polyalkylene polyamine composition of the present invention and a tertiary amine compound having at least one active hydrogen group in its molecule. Also, in the following Example 25, rigid polyurethane foam was produced by using the hydroxyalkylated polyalkylene polyamine composition of the present invention without using a tertiary amine compound having at least one active hydrogen group in its molecule. On the other hand, in the Comparative Examples 8 to 11, rigid polyurethane foam was produced without using the hydroxyalkylated polyalkylene polyamine composition of the present invention.

Premix C was prepared by using the amount of raw materials shown in Table 5.

TABLE 5

|  | Parts by weight (pbw) |
|---|---|
| Amine base polyol [1] | 0-40 |
| Sucrose base polyol [2] | 60-90 |
| Polyol [3] | 0-10 |
| Water | 5 |
| Lead catalyst [4] | 0-0.3 |
| Catalyst 1 [5] | 0-12 |
| Catalyst 2 [6] | 0-3 |
| Catalyst 3 [7] | 0-3 |
| Silicone foam stabilizer [8] | 1.5 |
| Flame retardant [9] | 20 |
| Isocyanate [10] | INDEX = 110 [11] |

[1] Amine base polyol (EXCENOL 450ED, product of Asahi Glass Co., Ltd.)
[2] Sucrose base polyol (SG 360, product of Takeda Pharmaceutical Company Limited)
[3] Hydroxyalkylated polyalkylene polyamine composition 6
[4] Lead octanoate, 20% lead solution (product of Nihon Kagaku Sangyo Co. Ltd.)
[5] Triethylene diamine 33.3% dipropylene glycol solution ("TEDA-L33E", a product of Tosoh Corporation)
[6] N'-(2-hydroxyethyl-N,N,N'-trimethyl-bis(2-aminoethyl)ether (synthetic composition)
[7] N,N,N'-trimethyl-N'-(2-hydroxyethyl)ethylene diamine (TOYOCAT, product of Tosoh Corporation)
[8] L5420, product of Dow Corning Toray Co. Ltd.
[9] Tris(chloropropyl) phosphate (TMCPP, product of Daihachi Chemical Industry Co. Ltd.)
[10] Polymeric MDI (MR200, product of Nippon Polyurethane Industry Co. Ltd.)
[11] INDEX = (No. of moles of NCO groups/No. of moles of OH groups) × 100

After 55 g of each Premix C shown in Table 5 was placed in a 300 ml of polyethylene cup, the temperature thereof was adjusted to be 8° C. An isocyanate solution, the temperature of which was adjusted to be 8° C. in a separate container, which makes the isocyanate Index (=isocyanate groups/OH groups (molar ratio)×100) to be 110 was added to the cup of Premix C, and rapidly stirred at 6000 rpm for 4 seconds by using an agitating device. The temperature of the mixed solution obtained by mixing and stirring was transferred to a 2 L polyethylene cup, the temperature of which had been adjusted to 23° C., and the reactivity during foaming was measured. After that, the core density of the molded foam was measured. Results are shown in Table 6.

TABLE 6

|  | Ex. 23 | Ex. 24 | Ex. 25 | C. Ex. 8 | C. Ex. 9 | C. Ex 10 | C. Ex 11 |
|---|---|---|---|---|---|---|---|
| Amount add (pbw) | | | | | | | |
| Amine base polyol | 30 | 30 | 30 | 40 | 40 | 40 | 40 |
| Sucrose base polyol | 60 | 60 | 60 | 60 | 60 | 60 | 60 |
| Polyol 6 | 10 | 10 | 10 | | | | |
| Lead catalyst | | | | 0.3 | | | |
| Catalyst 1 | 3 | 4 | 6.5 | 6.5 | 12 | 5.5 | 7 |
| Catalyst 2 | 2 | | | | | 3 | |
| Catalyst 3 | | 2 | | | | | 3 |
| Reactivity (sec) | | | | | | | |
| Cream Time | 6.9 | 7.3 | 8.2 | 9.5 | 10 | 7.2 | 7.7 |
| Gelling Time | 14 | 14 | 14 | 14 | 14 | 14 | 13 |
| Rise Time | 21 | 20 | 21 | 18 | 21 | 21 | 21 |
| Foam Properties | | | | | | | |
| Core Density (kg/m$^3$) | 27 | 26 | 27 | 41 | 24 | 28 | 23 |

Note that the measuring method of each item was as follows.

Cream time: start time of foaming and start time of rising foam were visually measured.

Gelling time: time required to change from a liquid-like substance to a resin-like substance by the reaction was visually measured.

Rise time: time when the rising of foam stopped was visually measured.

Core density: core portion of the foam was cut into a piece of 10 cm×10 cm×6 cm and the weight thereof measured to calculate its core density.

As is obvious from Table 6, in Examples 23 and 24 in which the hydroxyalkylated polyalkylene polyamine composition of the present invention and the general amine base polyol were used together with a tertiary amine compound having at least one active hydrogen in its molecule and triethylene diamine as catalyst, use of harmful lead catalyst as in Comparative Example 8 may be eliminated. Also, as compared to Comparative Example 9 in which no lead catalyst was used, the mount of volatile amine catalyst may be significantly as shown in Examples 23 and 24.

Also, as compared to Comparative Example 9 in which only triethylene diamine was used as a catalyst, the amount of volatile amine catalyst may be reduced as shown in Example 25. In Comparative Examples 10 and 11 in which a general amine base polyol was used, the amount of amine catalyst used was larger than that used in Examples 23 to 25, respectively.

INDUSTRIAL APPLICABILITY

Since the hydroxyalkylated polyalkylene polyamine composition of the present invention has a plurality of hydroxyl groups, a relatively high molecular weight, and catalytic activity, it becomes possible to reduce the amount of conventional amine catalyst used without deteriorating the physical properties of a polyurethane resin when the composition is used for the manufacturing method of the polyurethane. In addition, it becomes possible to obtain polyurethane products with excellent productivity and moldability at low cost without causing odor problems or toxic and environmental problems.

Also, according to the method of manufacturing rigid polyurethane foam of the present invention, it becomes possible to obtain rigid polyurethane foam products with excellent productivity without causing the above-mentioned odor problems or toxic and environmental problems.

The invention claimed is:

1. A method for preparing a polyurethane resin, comprising:
reacting a polyalkylene polyamine represented by a following general formula (4):

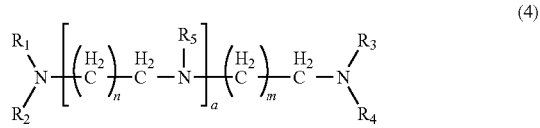

wherein $R_1$ to $R_4$ are hydrogen atoms; $R_5$ is a hydrogen atom or a $C_1$ to $C_3$ alkyl group; when $R_5$ is a $C_1$ to $C_3$ alkyl group, $R_5$ and $R_1$, $R_2$, $R_3$, or $R_4$ may arbitrarily bond together to form a ring; n and m are independently an integer from 1 to 5; and a is an integer from 1 to 6;

with an N-alkylating agent while varying a molar ratio of the polyalkylene polyamine to the N-alkylating agent to obtain at least two kinds of N-alkylated polyalkylenepolyamines;

adding an alkylene oxide to the at least two kinds of N-alkylated polyalkylene polyamines to obtain a hydroxyalkylated polyalkylene polyamine composition comprising at least two kinds of hydroxyalkylated polyalkylene polyamines represented by the following general formula (1):

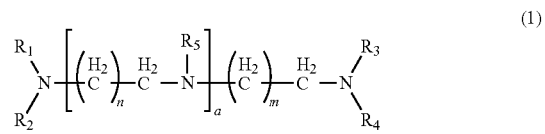

wherein $R_1$ to $R_5$ are independently a $C_1$ to $C_3$ alkyl group or a substituent represented by the following general formula (2):

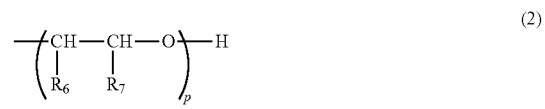

wherein $R_6$ and $R_7$ are independently a hydrogen atom or a $C_1$ to $C_4$ alkyl group, and p is an integer from 1 to 3, and $R_5$ and $R_1$, $R_2$, $R_3$, or $R_4$ may arbitrarily bond together to form a ring; at least one of $R_1$ to $R_5$ is a substituent represented by the general formula (2) but all of $R_1$ to $R_5$ cannot be substituents represented by the general formula (2) at the same time; n and m are independently an integer from 1 to 5; and a is an integer from 1 to 6; and reacting a polyol and an isocyanate in the presence of the hydroxyalkylated polyalkylene polyamine composition.

2. The method of claim 1, wherein the ratio of $C_1$ to $C_3$ alkyl groups to substituents represented by the general formula (2) among $R_1$ to $R_5$ in the general formula (1) is in the range of ($C_1$ to $C_3$ alkyl groups)/(substituents represented by the general formula (2))=80/20 to 20/80 (molar ratio).

3. The method of claim 1, wherein the hydroxyl value of the hydroxyalkylated polyalkylene polyamine is 20 to 800 mg KOH/g.

4. The method of claim 1, wherein the polyol comprises a polyether polyol, polyester polyol, polymer polyol, phosphorous containing polyol or halogen containing polyol.

5. The method of claim 1, wherein the polyol has an average hydroxyl value of about 20 to 1000 mg KOH/g.

6. The method of claim 1, wherein the isocyanate is selected from the group consisting of aromatic polyisocyanates, aliphatic polyisocyanates, cycloaliphatic polyisocyanates, and mixture thereof.

7. The method of claim 1, wherein the isocyanate is selected from the group consisting of toluene diisocyanate, diphenylmethane diisocyanate, naphthylene diisocyanate, xylene diisocyanate, hexamethylene diisocyanate, dicyclohexyl diisocyanate isophorone diisocyanate, and mixture thereof.

8. The method of claim 1, wherein the isocyanate is selected from the group consisting of toluene diisocyanate, diphenylmethane diisocyanate, and mixtures thereof.

9. The method of claim 1, wherein the mixing ratio of isocyante to polyol is 60 to 400 in terms of isocyanate index.

10. A method for preparing a polyurethane foam, comprising:
reacting a polyalkylene polyamine represented by a following general formula (4):

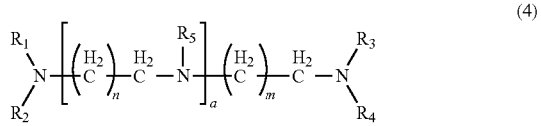

(4)

wherein $R_1$ to $R_4$ are hydrogen atoms; $R_5$ is a hydrogen atom or a $C_1$ to $C_3$ alkyl group; when $R_5$ is a $C_1$ to $C_3$ alkyl group, $R_5$ and $R_1$, $R_2$, $R_3$, or $R_4$ may arbitrarily bond together to form a ring; n and m are independently an integer from 1 to 5; and a is an integer from 1 to 6;
with an N-alkylating agent while varying a molar ratio of the polyalkylene polyamine to the N-alkylating agent to obtain at least two kinds of N-alkylated polyalkylene polyamines,
adding an alkylene oxide to the at least two kinds of N-alkylated polyalkylene polyamines to obtain a hydroxyalkylated polyalkylene polyamine composition comprising at least two kinds of hydroxyalkylated polyalkylene polyamines represented by the following general formula (1):

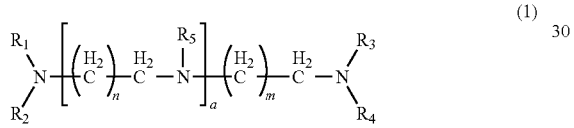

(1)

wherein $R_1$ to $R_5$ are independently a $C_1$ to $C_3$ alkyl group or a substituent represented by the following general formula (2):

(2)

wherein $R_6$ and $R_7$ are independently a hydrogen atom or a $C_1$ to $C_4$ alkyl group, and p is an integer from 1 to 3,
and $R_5$ and $R_1$, $R_2$, $R_3$, or $R_4$ may arbitrarily bond together to form a ring; at least one of $R_1$ to $R_5$ is a substituent represented by the general formula (2) but all of $R_1$ to $R_5$ cannot be substituents represented by the general formula (2) at the same time; n and m are independently an integer from 1 to 5; and a is an integer from 1 to 6; and
reacting a polyol and an isocyanate in the presence of a blowing agent and the hydroxyalkylated polyalkylene polyamine composition.

11. The method of claim 10, wherein the ratio of $C_1$ to $C_3$ alkyl groups to substituents represented by the general formula (2) among $R_1$ to $R_5$ in the general formula (1) is in the range of ($C_1$ to $C_3$ alkyl groups)/(substituents represented by the general formula (2))=80/20 to 20/80 (molar ratio).

12. The method of claim 10, wherein the hydroxyl value of the hydroxyalkylated polyalkylene polyamine is 20 to 800 mg KOH/g.

13. The method of claim 10, wherein the polyol comprises a polyether polyol, polyester polyol, polymer polyol, phosphorous containing polyol or halogen containing polyol.

14. The method of claim 10, wherein the polyol has an average hydroxyl value of about 20 to 1000 mg KOH/g.

15. The method of claim 10, wherein the isocyanate is selected from the group consisting of aromatic polyisocyanates, aliphatic polyisocyanates, cycloaliphatic polyisocyanates, and mixture thereof.

16. The method of claim 10, wherein the isocyanate is selected from the group consisting of toluene diisocyanate, diphenylmethane diisocyanate, naphthylene diisocyanate, xylene diisocyanate, hexamethylene diisocyanate, dicyclohexyl diisocyanate isophorone diisocyanate, and mixture thereof.

17. The method of claim 10, wherein the isocyanate is selected from the group consisting of toluene diisocyanate, diphenylmethane diisocyanate, and mixtures thereof.

18. The method of claim 10, wherein the mixing ratio of isocyante to polyol is 60 to 400 in terms of isocyanate index.

19. The method of claim 10, wherein blowing agent is water, an organic compound having a low boiling, or a mixture thereof.

20. A method for preparing a rigid polyurethane foam, comprising:
reacting a polyalkylene polyamine represented by a following general formula (4):

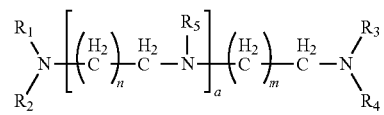

(4)

wherein $R_1$ to $R_4$ are hydrogen atoms; $R_5$ is a hydrogen atom or a $C_1$ to $C_3$ alkyl group; when $R_5$ is a $C_1$ to $C_3$ alkyl group, $R_5$ and $R_1$, $R_2$, $R_3$, or $R_4$ may arbitrarily bond together to form a ring; n and m are independently an integer from 1 to 5; and a is an integer from 1 to 6;
with an N-alkylating agent while varying a molar ratio of the polyalkylene polyamine to the N-alkylating agent to obtain at least two kinds of N-alkylated polyalkylene polyamines;
adding an alkylene oxide to the at least two kinds of N-alkylated polyalkylene polyamines to obtain a hydroxyalkylated polyalkylene polyamine composition comprising at least two kinds of hydroxyalkylated polyalkylene polyamines represented by the following general formula (1):

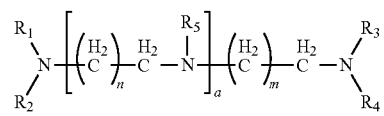

(1)

wherein $R_1$ to $R_5$ are independently a $C_1$ to $C_3$ alkyl group or a substituent represented by the following general formula (2):

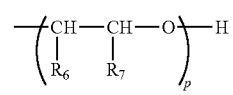

(2)

wherein $R_6$ and $R_7$ are independently a hydrogen atom or a $C_1$ to $C_4$ alkyl group, and p is an integer from 1 to 3, and $R_5$ and $R_1$, $R_2$, $R_3$, or $R_4$ may arbitrarily bond together to form a ring; at least one of $R_1$ to $R_5$ is a substituent represented by the general formula (2) but all of $R_1$ to $R_5$ cannot be substituents represented by the general formula (2) at the same time; n and m are independently an integer from 1 to 5; and a is an integer from 1 to 6; and reacting the hydroxyalkylated polyalkylene polyamine composition and isocyanate in the presence of water, a tertiary amine compound having at least one active hydrogen group and a foam stabilizing agent.

21. The method of claim 20, wherein the hydroxyl value of the hydroxyalkylated polyalkylene polyamine composition is from 100 to 800 mg KOH/g.

22. A method of claim 20, wherein the tertiary amine compound having at least one active hydrogen group in its molecule is selected from the group consisting of N'-(2-hydroxyethyl)-N,N,N'-trimethyl-bis(2-aminoethyl)ether, N,N-dimethyl hexanol amine, N,N-dimethylamino ethoxy ethanol, N,N,N'-trimethyl-N'-(2-hydroxyethyl)ethylenediamine, N-(2-hydroxyethyl)-N,N',N'',N'''-tetramethyldiethylenetriamine, N-(2-hydroxypropyl)-N,N',N'',N'''-tetramethyldiethylenetriamine, N,N,N'-trimethyl-N'-(2-hydroxyethyl)propanediamine, N-methyl-N'-(2-hydroxyethyl)piperazine, bis(N,N-dimethylaminopropyl)amine, bis(N,N-dimethylaminopropyl)isopropanolamine, 2-amino quinuclidine, 3-amino quinuclidine, 4-amino quinuclidine, 2-quinuclidiol, 3-quinuclidinol, 4-quinuclidinol, 1-(2'-hydroxypropyl)imidazole, 1-(2'-hydroxypropyl)-2-methylimidazole, 1-(2'-hydroxyethyl)imidazole, 1-(2'-hydroxyethyl)-2-methylimidazole, 1-(2'-hydroxypropyl)-2-methylimidazole, 1-(3'-aminopropyl)imidazole, 1-(3'-aminopropyl)-2-methylimidazole, 1-(3'-hydroxypropyl)imidazole, 1-(3'-hydroxypropyl)-2-methylimidazole, N,N-dimethylaminopropyl-N'-(2-hydroxyethyl)amine, N,N-dimethylaminopropyl-N',N'-bis(2-hydroxyethyl)amine, N,N-dimethylaminopropyl-N',N'-bis(2-hydroxypropyl)amine, N,N-dimethylaminoethyl-N',N'-bis(2-hydroxyethyl)amine, and N,N-dimethylaminoethyl-N',N'-bis(2-hydroxypropyl)amine.

23. The method of claim 20, wherein the tertiary amine compound having at least one active hydrogen group in its molecule is selected from the group consisting of N'-(2-hydroxyethyl)-N,N,N'-trimethyl-bis(2-aminoethyl)ether, N,N-dimethylaminoethoxyethanol, N,N,N'-trimethyl-N'-(2-hydroxyethyl)ethylenediamine, N-(2-hydroxyethyl)-N,N',N'', N''-tetramethyldiethylenetriamine, N-(2-hydroxypropyl)-N,N', N'',N''-amine, and bis(N,N-dimethylaminopropyl)isopropanolamine.

24. The method of claim 20, wherein the rigid polyurethane foam is a spray-type rigid polyurethane foam.

* * * * *